United States Patent
Nan et al.

(10) Patent No.: US 9,353,048 B2
(45) Date of Patent: May 31, 2016

(54) COMPOUND AS KCNQ POTASSIUM CHANNEL AGONIST, PREPARATION METHOD THEREFOR AND USE THEREOF

(71) Applicant: SHANGHAI INSTITUTE OF MATERIA MEDICA, CHINESE ACADEMY OF SCIENCES, Shanghai (CN)

(72) Inventors: Fajun Nan, Shanghai (CN); Min Li, Shanghai (CN); Zhaobing Gao, Shanghai (CN); Fei Chen, Shanghai (CN); Yangming Zhang, Shanghai (CN); Pingzheng Zhou, Shanghai (CN); Haining Hu, Shanghai (CN); Haiyan Xu, Shanghai (CN); Sheng Liu, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 14/353,842

(22) PCT Filed: Oct. 23, 2012

(86) PCT No.: PCT/CN2012/001423
§ 371 (c)(1),
(2) Date: Apr. 24, 2014

(87) PCT Pub. No.: WO2013/060097
PCT Pub. Date: May 2, 2013

(65) Prior Publication Data
US 2014/0336252 A1    Nov. 13, 2014

(30) Foreign Application Priority Data

Oct. 25, 2011    (CN) .......................... 2011 1 0328036

(51) Int. Cl.
| | | |
|---|---|---|
| C07C 261/00 | (2006.01) | |
| C07C 271/28 | (2006.01) | |
| C07D 235/26 | (2006.01) | |
| C07C 233/43 | (2006.01) | |
| C07C 231/00 | (2006.01) | |
| C07C 233/44 | (2006.01) | |
| C07C 269/04 | (2006.01) | |

(52) U.S. Cl.
CPC ............. *C07C 271/28* (2013.01); *C07C 231/00* (2013.01); *C07C 233/43* (2013.01); *C07C 233/44* (2013.01); *C07C 269/04* (2013.01); *C07D 235/26* (2013.01); *C07C 2101/16* (2013.01)

(58) Field of Classification Search
CPC    C07C 2101/16; C07C 231/00; C07C 233/43; C07C 233/44; C07C 269/04; C07C 271/28; C07D 235/26
See application file for complete search history.

(56) References Cited

U.S. PATENT DOCUMENTS

| | | | |
|---|---|---|---|
| 5,384,330 A | 1/1995 | Dieter et al. | |
| 5,852,053 A | 12/1998 | Rostock et al. | |
| 7,718,671 B2 * | 5/2010 | Phadke et al. | ................ 514/307 |

FOREIGN PATENT DOCUMENTS

| | | | |
|---|---|---|---|
| CN | 1761464 A | | 4/2006 |
| WO | WO2004/082677 | * | 9/2004 |
| WO | 2011/012659 A2 | | 2/2011 |

OTHER PUBLICATIONS

STN 2004 A, (2004).*
English translation of International Search Report corresponding to PCT/CN2012/001423 mailed Jan. 24, 2013 (5 pages).
RN: 940364-09-0; Registry ED Entered STN (Jul. 1, 2007); CN: Acetamide, N-[4-[[(4-fluorophenyl)methyl]amino]phenyl]-.

* cited by examiner

*Primary Examiner* — Yevegeny Valenrod
*Assistant Examiner* — Blaine G Doletski
(74) *Attorney, Agent, or Firm* — Kilpatrick Townsend & Stockton LLP

(57) ABSTRACT

The present invention provides compounds having the structure represented by general formula I, pharmaceutically acceptable salts thereofagonist, preparation methods therefor and a use thereof in the preparation of a medicine for the treatment of nervous system diseases. The compounds or pharmaceutical compositions thereof can be used as the KCNQ potassium channel agonist for treating nervous system diseases. Compared to retigabine, a compound in the prior art, the compound of the present invention have the same or better therapeutic effect, are easier for synthesis and storage, and less prone to oxidate deterioration.

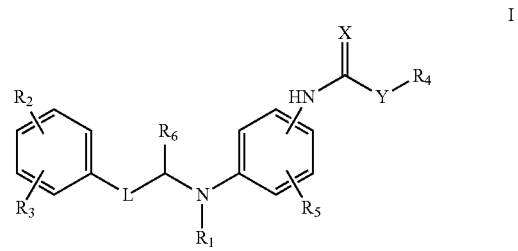

4 Claims, No Drawings

COMPOUND AS KCNQ POTASSIUM CHANNEL AGONIST, PREPARATION METHOD THEREFOR AND USE THEREOF

TECHNICAL FIELD

The present invention belongs to the field of pharmacy. In particular, the present invention relates to a class of novel compounds agonist which can be used as potassium ion channels agonist, the preparation method thereof, and the use of the compounds agonist or the pharmaceutically acceptable salts thereof or the pharmaceutical composition thereof in the preparation of medicaments for treating nervous system diseases, such as epilepsy, convulsion, neuropathic pain, acute ischemic stroke or neurodegenerative diseases.

BACKGROUND

Epilepsy is a syndrome of neurological function disorder resulted from paroxysmal and abnormal discharging of brain neurons, which has disturbances in motion, sensation, consciousness, mental condition and vegetative nervous system. The incidence rate of epilepsy is approximately 1%, which severely threatening life and health of mankind. The neurological electrophysiological basis for epilepsy is excessive and synchronous discharging of neurons, i.e. epileptiform discharging, which mainly results from excitatory disorder of neurons. The neuronal excitability is determined on the balance of activities of potassium ion channels, sodium ion channels and calcium ion channels. If such balance is disturbed, neuronal excitability disorder and further epilepsy seizures are likely to happen.

Potassium ion channels play an important role in adjustment of neuronal excitation, wherein the ionic mechanism is that in concentration of potassium ions in cells is higher than that out of cells, when the depolarization of membrane potential occurs, potassium ion channels are activated, therefore, potassium ions having positive charges outflow off cells, such that membrane potential becomes negative (polarization or hyperpolarization) and neuronal excitability decreases. Recently, genetic research on epilepsy declares that abnormality of potassium ion channels will directly lead to epilepsy (Wulff, H. Et al. Chem Rev 2008, 108 (5), 1744-73.), such as benign familial neonatal convulsions (BFNC).

Besides to protein kinase and G-protein coupled receptor, voltage-gated ion channels (VGICs) is the third kind of signal transduction molecules (Harmar, A. J. et al., Nucleic Acids Res 2009, 37 (Database issue), D680-5.). Among voltage-gated ion channels' 78 of family members, more than a half are potassium ion channels, which are divided into 4 types according to their function and structural features: inward rectifier potassium ion channels ($K_{ir}$); two pore potassium ion channels ($K_{2p}$); $Ca^{2+}$-activated potassium ion channels ($K_{Ca}$) and voltage-gated potassium ion channels ($K_V$) (Wulff, H. et al., Nat Rev Medicament Discov 2009, 8 (12), 982-1001.).

Voltage-gated potassium ion channels ($K_V$) is an important member of potassium ion channels superfamily, which has 12 members ($K_V1.X$-$K_V12.X$). Wherein, KCNQ channels is the $7^{th}$ member of the voltage-gated potassium ion channels (Kv7), which includes five subtypes, namely, KCNQ1 to KCNQ5. Compared with other potassium ion channels, the activation threshold of KCNQ channels is low, in other words, KCNQ channels can be opened at a voltage lower than action potential threshold (−60 mV), KCNQ channels has an slow activation process and will not inactivated on persistent depolarization. Those characters endow KCNQ channels with a basal level in adjustment of cellular excitability. The opening of KCNQ channels may decrease the cellular excitability, while inhibiting them will evoke membrane potential depolarization of neurocytes, such that the excitability is increased and more neural impulses are evoked.

Based on the said advantageous of KCNQ-targeted sites, the agonist thereof is deemed to be an effective medicament for treating epilepsy. By activating potassium ion channels to decrease neuronal excitability, such agonists of potassium ion channels not only can be used in treatment of epilepsy but also can be used in treatment of other diseases induced by exorbitant neuronal excitability, such as convulsion, neuropathic pain, acute ischemic stroke or neurodegenerative diseases.

Reported KCNQ agonists are mainly as follows.

1) A compound of following structure is disclosed in U.S. Pat. No. 5,384,330, which characterized in that it has a benzene ring substituted by two amino groups at positions next to each other.

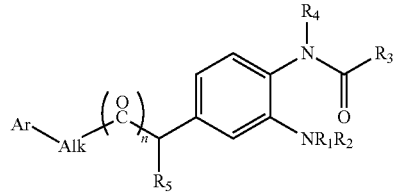

2) Agonists of KCNQ channels having following structure are described in Patent No. WO2005/087754 A1, which characterized in that it has a benzene ring substituted by two amino groups at positions opposite to each other, wherein, the nitrogen atom in one of the amino group is in a saturated ring (or a heterocycle when W is O), while the two hydrogen atoms at the positions next to another nitrogen atom on the benzene ring are substituted by $R_1$ or $R_2$.

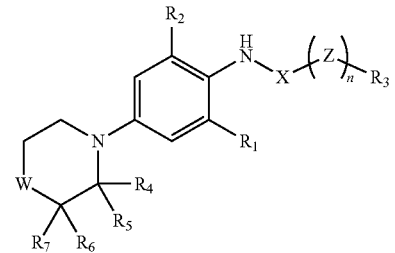

3) Patent No. WO2008024398-B1 records compound of following structure, which has a similar structure to that of compounds in Patent No. WO2005/087754, except for an additional ring fused to the saturated ring.

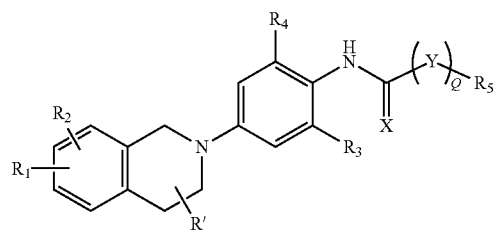

At present, the most representative KCNQ agonist is commercially available retigabine having following structure, which is an anti-epilepsy medicament developed by GSK (GlaxoSmithKline):

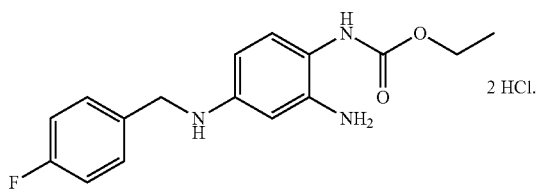 [SMILES: CCOC(=O)Nc1ccc(NCc2ccc(F)cc2)cc1N]

Retigabine is the first KCNQ agonist, which has been investigated in a systematic procedure. By activating KCNQ2-5, retigabine is mainly used for treatment of adults suffered from partial seizures of epilepsy. Retigabine can be absorbed in short time, its maximum concentration in plasma will be reached 1.5 h to 2 h after administration of single dosage.

Retigabine has an electron-rich benzene ring substituted by three nitrogen atoms, wherein two nitrogen atoms are at positions next to each other, and one nitrogen atom is present in the form of amino. Such structural feature causes retigabine to be oxidized and deteriorated in synthesis and storage. In addition, the inventors of the present invention have found that the concentration of retigabine in mice's brain tissue is not high in research on tissue distribution of the medicament, which may influence the maximum effectiveness thereof. Thereby, it is necessary to develop an agonist of potassium ion channels, which has higher activity and more stable property, especially contributes to increase the concentration distribution in brain tissue, so as to be used in developing of medicaments for treating neuropathic diseases, such as epilepsy, convulsion, neuropathic pain, acute ischemic stroke or neurodegenerative diseases.

The inventors of the present application also find that when the nitrogen atom in —NH-(secondary amine) of retigabine is further substituted, the resulting compound not only retains or increase the retigabine's activity of opening potassium ion channels, but also has a higher distribution concentration in brain tissue than that of retigabine. Consequently, the compound of the present invention exhibits a better treatment effect.

SUMMARY OF THE INVENTION

One object of the present invention is to provide a class of novel compounds or pharmaceutically acceptable salts thereof which can be used as agonists of KCNQ potassium channels.

Another object of the present invention is to provide a method for preparing the compounds said above.

Yet another object of the present invention is to provide a pharmaceutical composition comprising the compounds or pharmaceutically acceptable salt thereof as an active ingredient and pharmaceutically acceptable auxiliary substances.

Still another object of the present invention is to provide a use of the compounds, pharmaceutically acceptable salt thereof or pharmaceutical composition thereof in preparing medicaments for treating nervous system diseases etc.

The compounds according to the present invention have the structure of following general formula I:

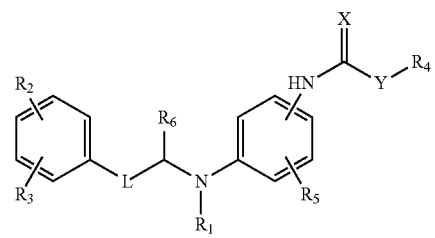

wherein,

L is not present, or L is a linking radical selected from the group consisting of

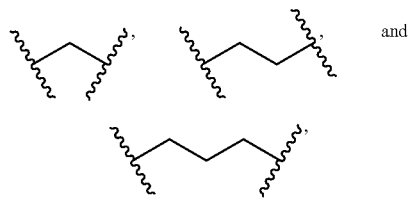

optionally substituted by $C_1$-$C_4$ alkyl;

$R_1$ is a radical selected from the group consisting of H, $C_1$-$C_6$ alkyl, $C_3$-$C_6$ cycloalkyl, $C_1$-$C_6$ alkylcarbonyl, $C_1$-$C_6$ alkoxycarbonyl, $C_1$-$C_6$ alkylamino carbonyl, $C_2$-$C_8$ alkenyl, $C_5$-$C_7$ cycloalkenyl, $C_2$-$C_8$ alkynyl and $C_6$-$C_{10}$ aryl; wherein, the $C_1$-$C_6$ alkyl is unsubstituted or optionally substituted by hydroxyl, amino, $C_1$-$C_4$ alkoxyl, $C_1$-$C_4$ alkylcarbonyl, halogen atom, $C_6$-$C_{10}$ aryl or halogenated $C_6$-$C_{10}$ aryl; the $C_2$-$C_8$ alkenyl is unsubstituted or optionally substituted by hydroxyl, amino, $C_1$-$C_4$ alkylcarbonyl, $C_1$-$C_4$ alkoxyl, halogen atom, $C_6$-$C_{10}$ aryl or halogenated $C_6$-$C_{10}$ aryl; and the $C_2$-$C_8$ alkynyl is unsubstituted or optionally substituted by hydroxyl, amino, $C_1$-$C_4$ alkylcarbonyl, $C_1$-$C_4$ alkoxyl, halogen atom, $C_6$-$C_{10}$ aryl or halogenated $C_6$-$C_{10}$ aryl;

$R_2$ is a radical selected from the group consisting of halogen atom and $C_1$-$C_4$ alkoxyl;

$R_3$ is a radical selected from the group consisting of H, halogen atom, trifluoromethyl, cyano, nitro, $C_1$-$C_4$ alkylcarbonyl and $C_1$-$C_4$ alkoxycarbonyl;

X is O, S or NH;

Y is not present, or Y is O or $NR_7$, wherein $R_7$ is a radical selected from the group consisting of H, $C_1$-$C_6$ alkyl, $C_2$-$C_6$ alkenyl, $C_2$-$C_6$ alkynyl and $C_3$-$C_8$ cycloalkyl;

$R_4$ is a radical selected from the group consisting of $C_1$-$C_6$ alkyl, $C_2$-$C_6$ alkenyl, $C_2$-$C_6$ alkynyl and $C_6$-$C_{10}$ aryl;

$R_5$ is a radical selected from the group consisting of H, halogen atom, amino, $C_1$-$C_6$ alkylamino and

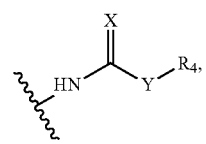

or R$_5$, together with adjacent

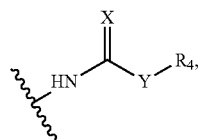

forms a fused-ring structure of

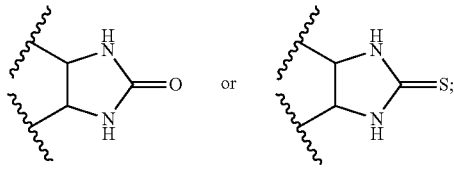 [SMILES: *C1NC(=O)NC1* ; "or" ; *C1NC(=S)NC1*]

R$_6$ is H, C$_1$-C$_6$ alkyl or C$_3$-C$_6$ cycloalkyl;

in the above said definitions of substituents, the halogen atom or the halogen atom in halogenated group is F, Cl or Br, and the halogenated radical is one substituted by F, Cl or Br.

More preferably, the compounds according to the present invention have a structure of general formula:

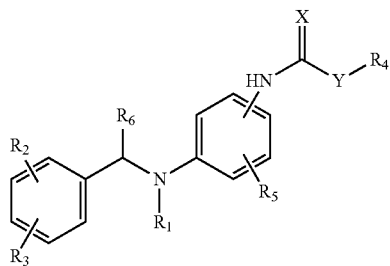

II wherein,

R$_1$ is a radical selected from the group consisting of H, C$_1$-C$_6$ alkyl, C$_3$-C$_6$ cycloalkyl, C$_1$-C$_6$ alkylcarbonyl, C$_1$-C$_6$ alkoxycarbonyl, C$_1$-C$_6$ alkylaminocarbonyl, C$_2$-C$_8$ alkenyl, C$_5$-C$_7$ cycloalkenyl, C$_2$-C$_8$ alkynyl and C$_6$-C$_{10}$ aryl; wherein, the C$_1$-C$_6$ alkyl is unsubstituted or optionally substituted by hydroxyl, amino, C$_1$-C$_4$ alkylcarbonyl, halogen atom, C$_6$-C$_{10}$ aryl or halogenated C$_6$-C$_{10}$ aryl; the C$_2$-C$_8$ alkenyl is unsubstituted or optionally substituted by hydroxyl, amino, C$_1$-C$_4$ alkylcarbonyl, C$_1$-C$_4$ alkoxyl, halogen atom, C$_6$-C$_{10}$ aryl or halogenated C$_6$-C$_{10}$ aryl; the C$_2$-C$_8$ alkynyl is unsubstituted or optionally substituted by hydroxyl, amino, alkylcarbonyl, C$_1$-C$_4$ alkoxyl, halogen atom, C$_6$-C$_{10}$ aryl or halogenated C$_6$-C$_{10}$ aryl;

R$_2$ is a radical selected from the group consisting of halogen atom and C$_1$-C$_4$ alkoxyl;

R$_3$ is a radical selected from the group consisting of H, halogen atom, trifluoromethyl and nitro;

X is O;

Y is not present or Y is O;

R$_4$ is a radical selected from the group consisting of C$_1$-C$_6$ alkyl, C$_2$-C$_6$ alkenyl, C$_2$-C$_6$ alkynyl and C$_6$-C$_{10}$ aryl;

R$_5$ is a radical selected from the group consisting of H, halogen atom, amino and

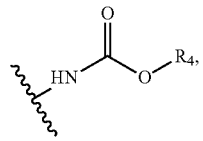

or R$_5$, together with adjacent

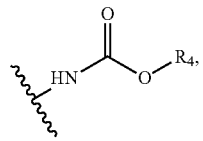

forms a fused-ring structure of

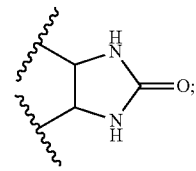 [SMILES: *C1NC(=O)NC1*]

R$_6$ is H, C$_1$-C$_6$ alkyl or C$_3$-C$_6$ cycloalkyl;

in the above said definitions of substituents, the halogen atom or the halogen atom in halogenated group is F, Cl or Br.

Most preferably, the compounds according to the present invention have a structure of general formula III:

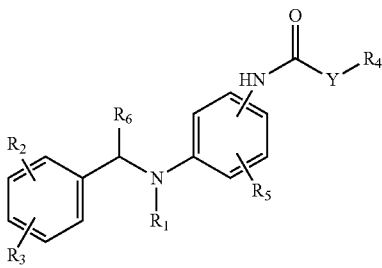

III wherein,

R$_1$ is a radical selected from the group consisting of H, C$_1$-C$_6$ alkyl, C$_2$-C$_8$ alkenyl, C$_5$-C$_7$ cycloalkenyl and C$_2$-C$_8$ alkynyl; wherein, the C$_1$-C$_6$ alkyl is unsubstituted or optionally substituted by hydroxyl, amino, C$_1$-C$_4$ alkylcarbonyl, halogen atom, phenyl or halogenated phenyl; the C$_2$-C$_8$ alkenyl is unsubstituted or optionally substituted by hydroxyl, amino, halogen atom, phenyl or halogenated phenyl; the C$_2$-C$_8$ alkynyl is unsubstituted or optionally substituted by hydroxyl, amino, halogen atom, phenyl or halogenated phenyl;

$R_2$ is a radical selected from the group consisting of F, Cl and methoxyl;

$R_3$ is a radical selected from the group consisting of H, halogen atom and trifluoromethyl;

Y is not present or Y is O;

$R_4$ is a radical selected from the group consisting of $C_1$-$C_6$ alkyl, $C_2$-$C_6$ alkenyl, $C_2$-$C_6$ alkynyl and $C_6$-$C_{10}$ aryl;

$R_5$ is a radical selected from the group consisting of H, halogen atom, amino and

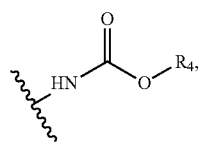

or $R_5$, together with adjacent

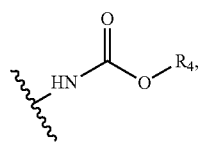

forms a fused-ring structure of

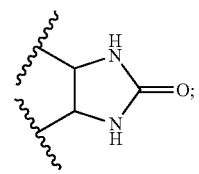 [SMILES: *C1NC(=O)NC1*]

$R_6$ is H or $C_1$-$C_6$ alkyl.

According to the most preferable embodiments, parts of the representative compounds are listed as follows:

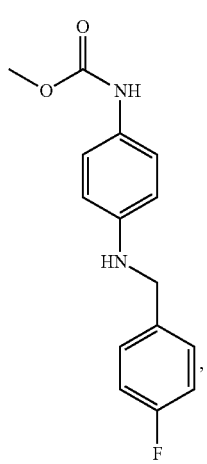
K1

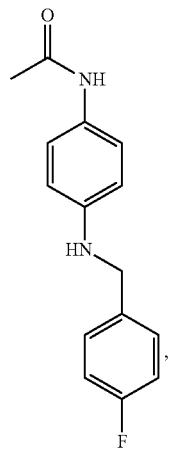
K2

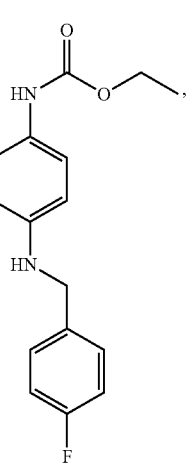
K3

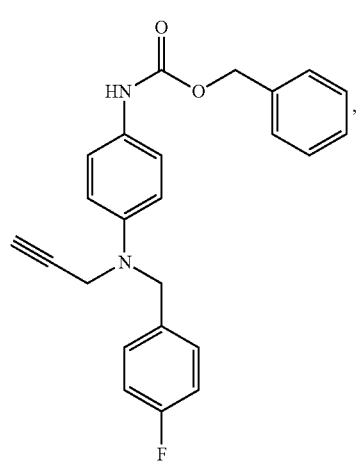
K4

-continued
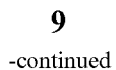
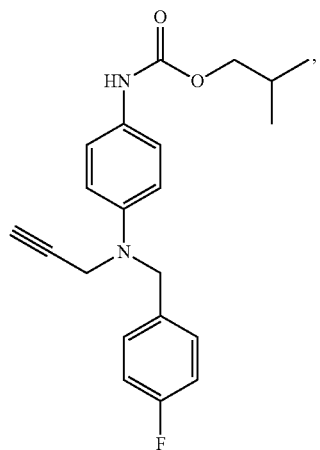
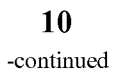
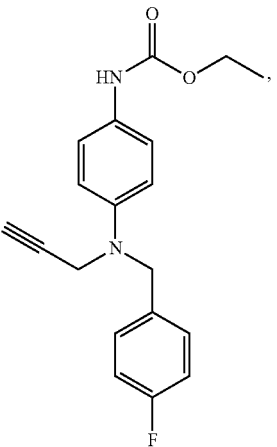
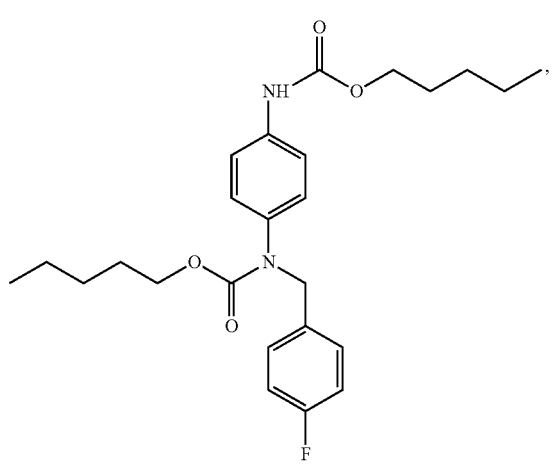
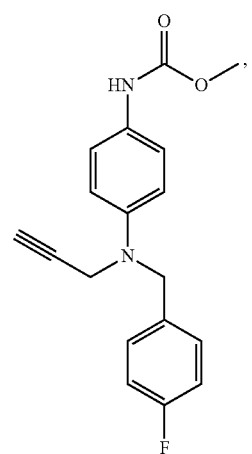
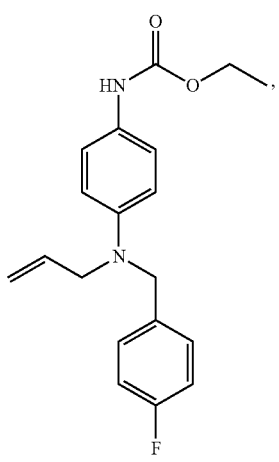
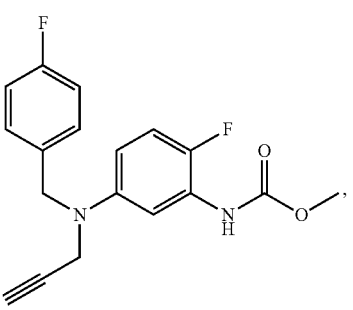
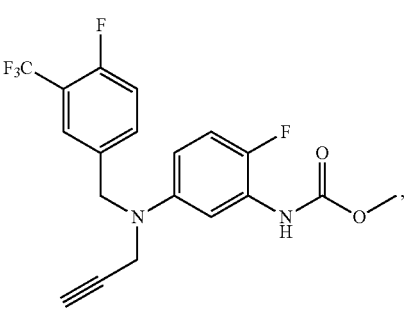

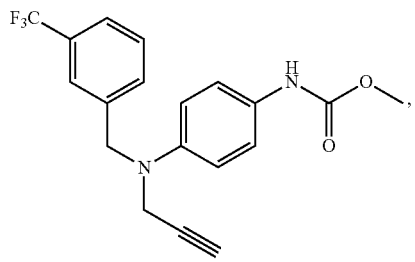
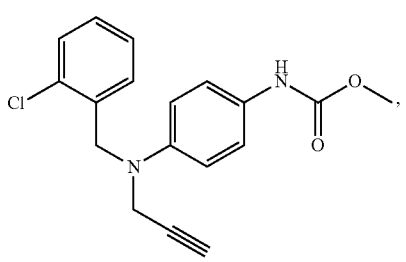

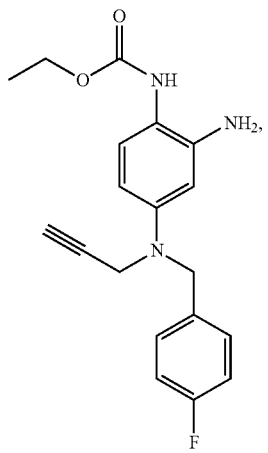
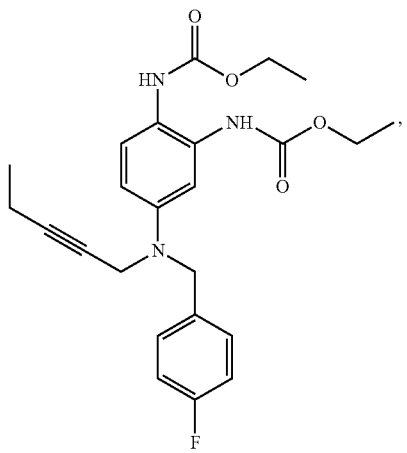

K28 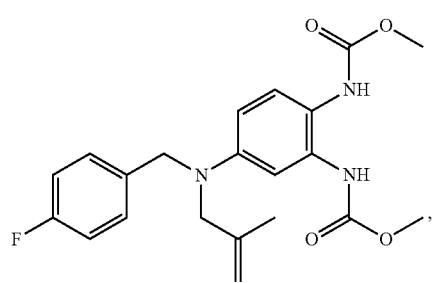
K29 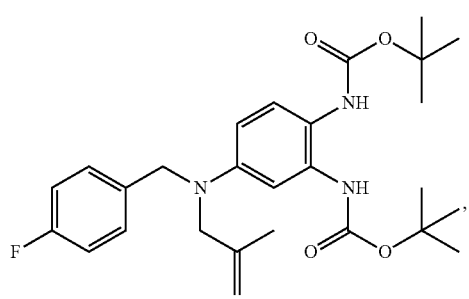
K30 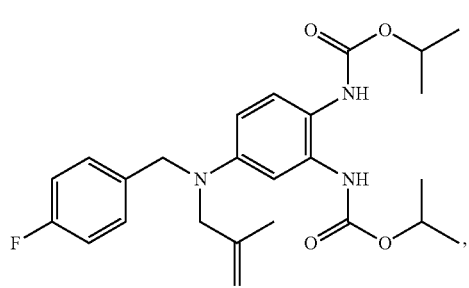
K31 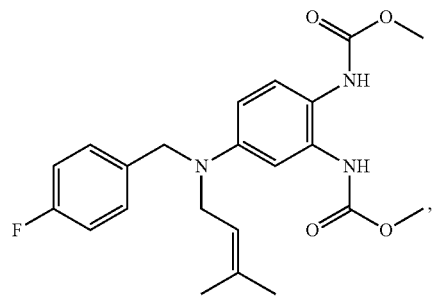
K32 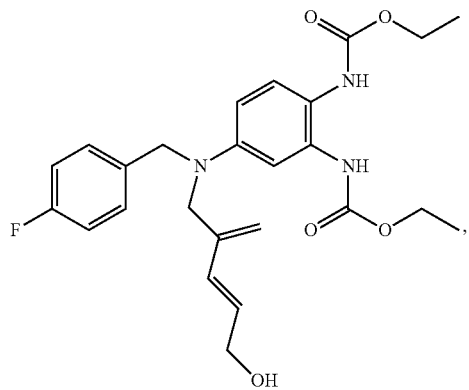
K33 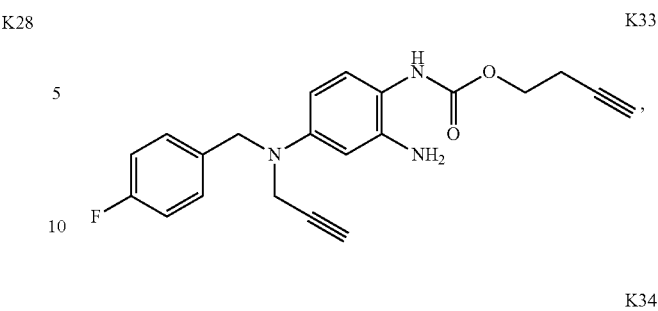
K34 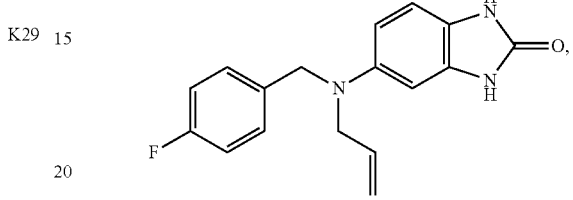
K35 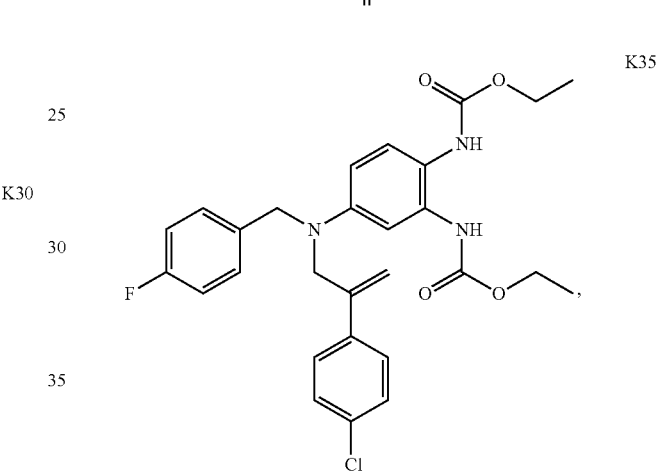
K36 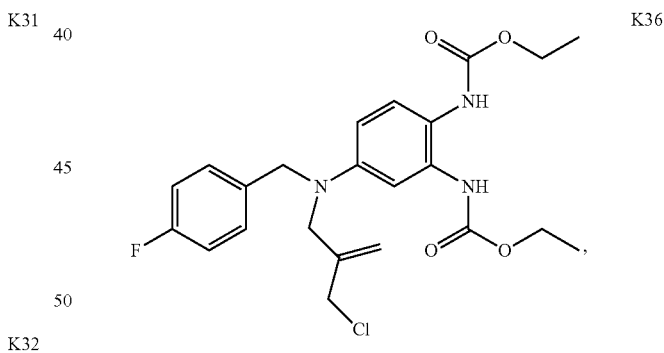
K37 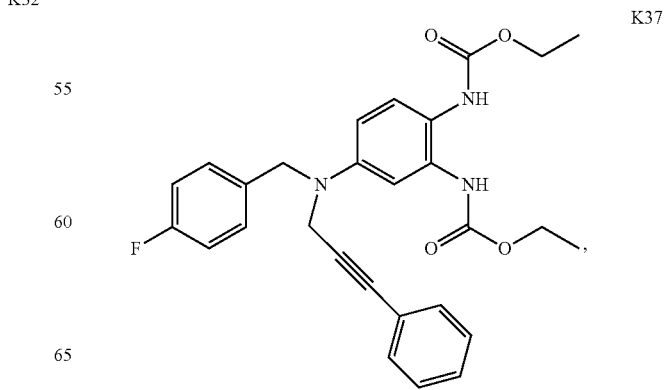

-continued

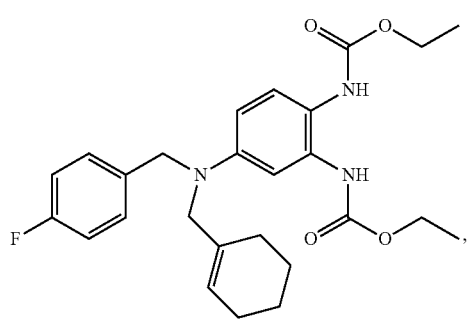

K38

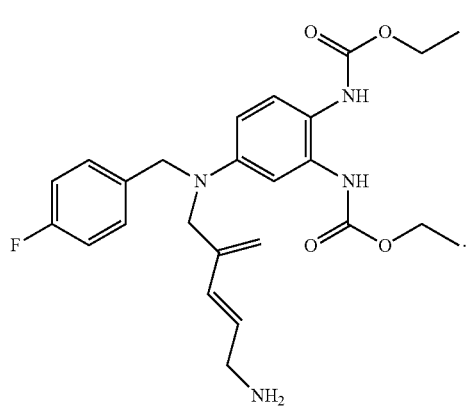

K39

Pharmaceutically acceptable salts of the above compounds according to the present invention are salts formed by the above compounds with an acid, and the acid is selected from the group consisting of maleic acid, succinic acid, citric acid, tartaric acid, fumaric acid, formic acid, acetic acid, propanoic acid, propandioic acid, oxalic acid, benzoic acid, phthalic acid, methanesulfonic acid, benzenesulfonic acid, toluenesulfonic acid, naphthalenesulfonic acid, 1,5-naphthalenedisulfonic acid, camphoric acid, camphor sulfonic acid, salicylic acid, acetyl salicylic acid, aspartic acid, glutamic acid, lactic acid, gluconic acid, ascorbic acid, gallic acid, amygdalic acid, malic acid, sorbic acid, trifluoroacetic acid, taurine, homotaurine, isethionic acid, cinnamic acid, hydrochloric acid, hydrobromic acid, hydroiodic acid, sulfuric acid, nitric acid, phosphoric acid and perchloric acid.

In another object of the present invention, methods for preparing the above compounds or pharmaceutically acceptable salts thereof are provided, comprising the following schemes, wherein P is an optional protection group of amino. For particulars, Protective Groups in Organic Synthesis (Organic Chemical teaching and researching group of East China University of Science & Technology, East China University of Science & Technology press) can be referred to.

Scheme 1:

Under catalysis of a weak acid, such as p-toluenesulfonic acid, carbonyl compound a reacts with phenylamine compound b for conducting a condensation reaction, thereby producing imine compound C. Imine compound C is reduced to secondary amine compound d under a such as sodium borohydride. Substituent $R_1$ is introduced into secondary amine compound d to produce intermediate compound f by a substitution reaction with halogenated hydrocarbon, or an addition reaction or an acylation reaction with α,β-unsaturated carbonyl compound. The protection group of amino group on intermediate compound d or f is removed to produce intermediate amine compound f or g at conditions well known to a person skilled in the art, and a compound of formula I is obtained by reacting amine f or g with an acylating agent of

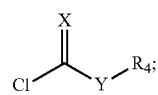

Scheme 1

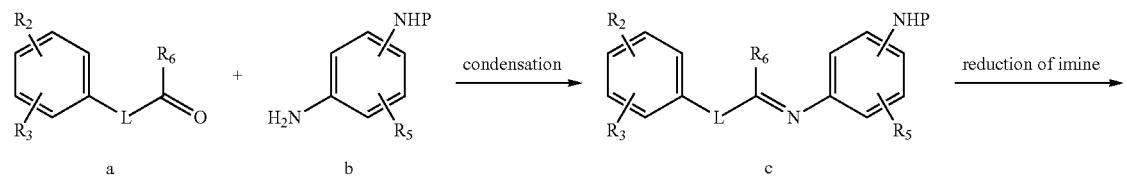

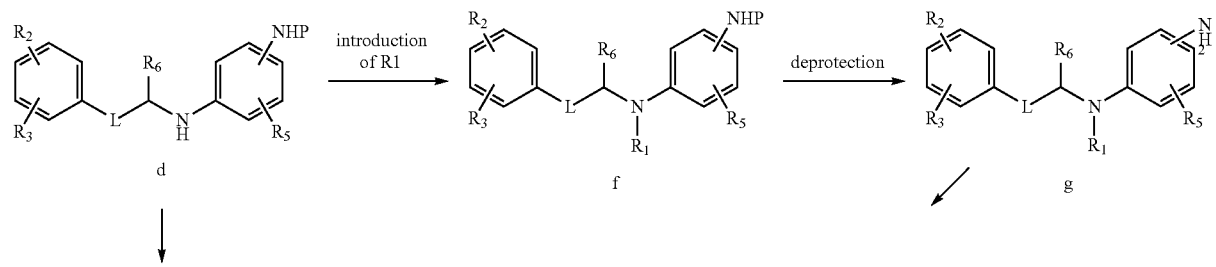

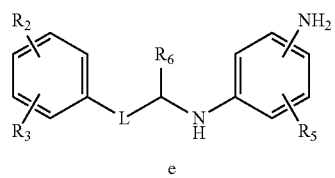 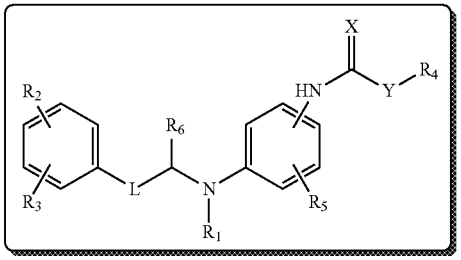

Scheme 2

Under catalysis of a weak acid, such as p-toluenesulfonic acid, carbonyl compound a reacts with nitro-substituted benzene diamines compound h for conducting a condensation reaction, thereby producing imine compound i. Imine compound i is reduced to intermediate amine j under a reducing agent such as sodium borohydride. Diamino intermediate k is obtained by reducing the nitro on amine intermediate j in a manner well known to a person skilled in the art, such as catalyzing hydrogenation with Pd—C or reducing with $SnCl_2$ (stannous chloride). Intermediate l is obtained by introducing two protection groups P of amino group. Intermediate m is obtained by introducing substituent $R_1$ using a method similar to that of scheme 1. Intermediate n is obtained by removing two protection groups P to expose two amino groups. Finally, a compound of formula I is obtained by reacting intermediate n with an acylating agent of

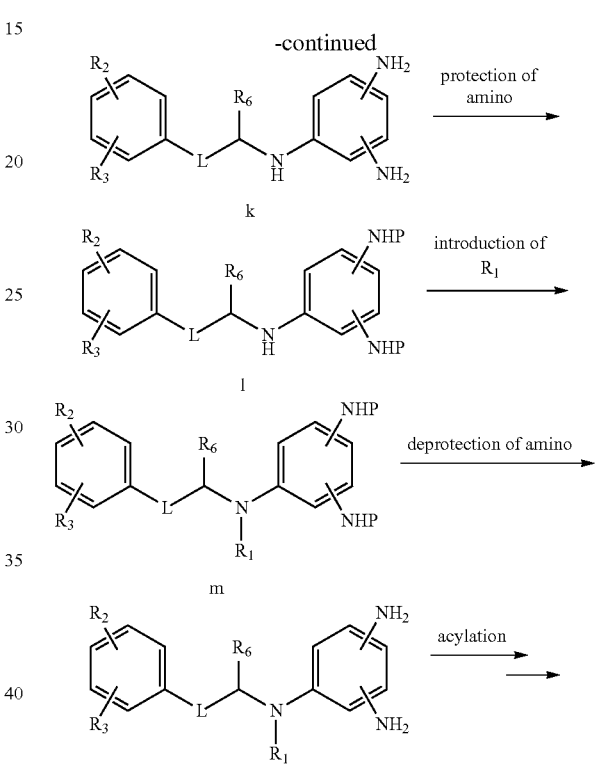

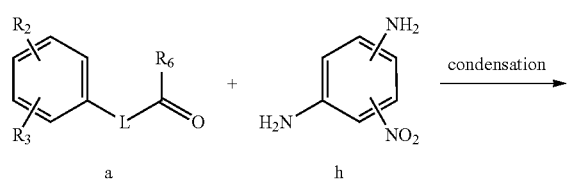

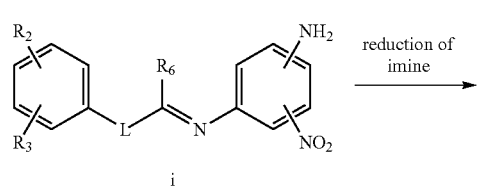

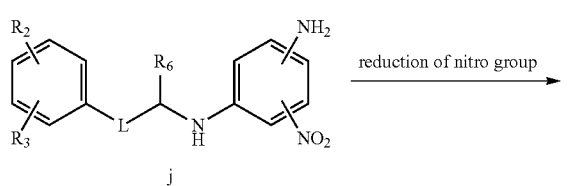

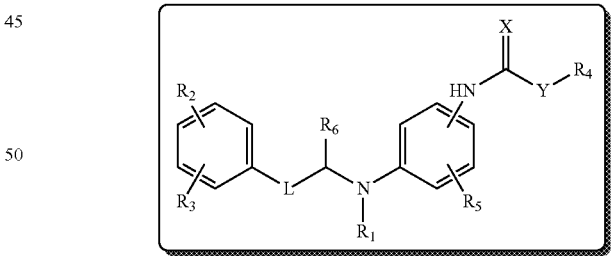

Scheme 3:

Intermediate compound p is obtained by reacting an acylating agent of

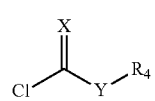

with nitro-substituted benzene amines compound o. Intermediate r is obtained by introducing substituent $R_1$ into amino compound q which is obtained by reducing nitro on intermediate compound p. Finally, a compound of formula I is obtained by reacting intermediate compound r with halogenated hydrocarbon of

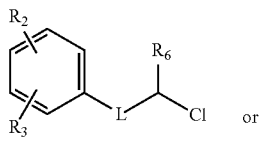

or

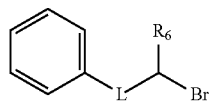

through a substitution reaction:

Scheme 3

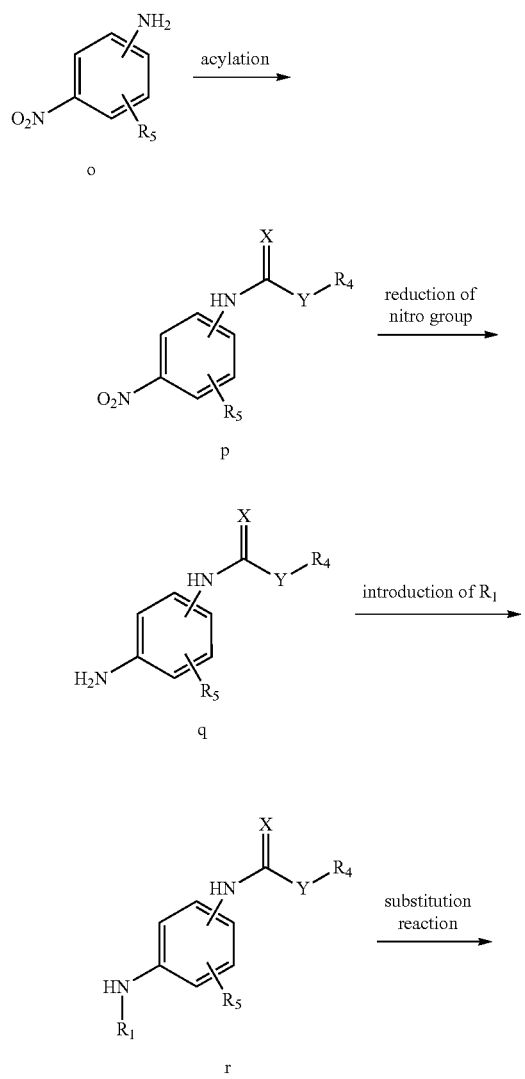

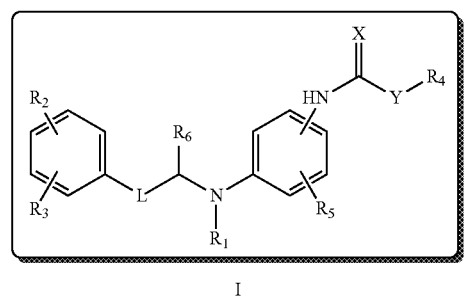

I

Scheme 4:

when substituent $R_1$ in the compound of general formula I is an alkenyl or alkynyl, other compounds of formula I according to the present invention can be obtained by olefin metathesis. The conventional olefin metathesis is a recombination reaction between olefins and olefins, or between olefins and alkines under catalysis of metal ruthenium carbene complex (Grubbs catalyst). The scheme of the olefin metathesis is shown as follows:

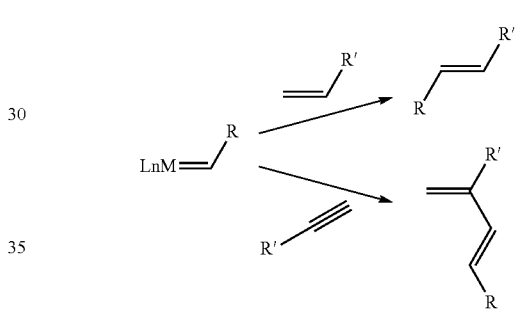

Scheme 5: Preparation for Salts of the Compounds

The compound of general formula I according to the present invention can be converted into pharmaceutically acceptable salts, such as hydrochloride, by adding a solution of acid into solution of the compound and completely removing solvent under reduced pressure.

In still another aspect of the present invention, a use of the above compounds, pharmaceutically acceptable salts or pharmaceutical composition thereof in preparing medicaments for the treatment of nervous system diseases, etc, is provided.

The nervous system diseases include epilepsy, convulsion, neuropathic pain, acute ischemic stroke or neurodegenerative diseases.

Advantageous Effects

Compared with existing medicaments, such as retigabine, the novel compounds described in the present invention are more stable and will not be readily oxidized and deteriorated.

Moreover, the compound provided by the present invention not only retains the high activity of activating potassium ion channels, which are the same as that of retigabine, but also exhibits a significant anti-epileptic action in vivo and high distribution concentration in brain tissue so as to achieve better therapeutic effects.

BEST MODE FOR CARRYING OUT THE INVENTION

The present invention will be further illustrated based on the following examples, but the present invention will not be limited thereto.

I. Preparation Examples for Compounds

In following preparation examples, NMR was conducted on a Mercury-Vx 300M instrument manufactured by Varian with calibration of δH 7.26 ppm (CDCl$_3$), 2.50 ppm (DMSO-d$_6$) and 3.15 ppm (CD$_3$OD). The reagents were mainly provided by Shanghai Chemical Reagent Co. Ltd and the silicone plates (model HSGF 254) for TLC thin layer chromatography were manufactured by Huiyou Silica gel Development Co. Ltd, Yantai, Shandong. The products were purified by normal phase column chromatography with a silica gel (model zcx-11) of 200-300 mesh, wherein, the silica gel was manufactured by Branch of Qingdao Haiyang Chemical Co. Ltd.

Preparation Example 1

Synthesis of methyl 4-(N-parafluorobenzyl-imino)-aniline acid methyl ester (K1)

1.1. Synthesis of tert-butyl 4-(N-parafluorobenzyl-imino)-aniline formate

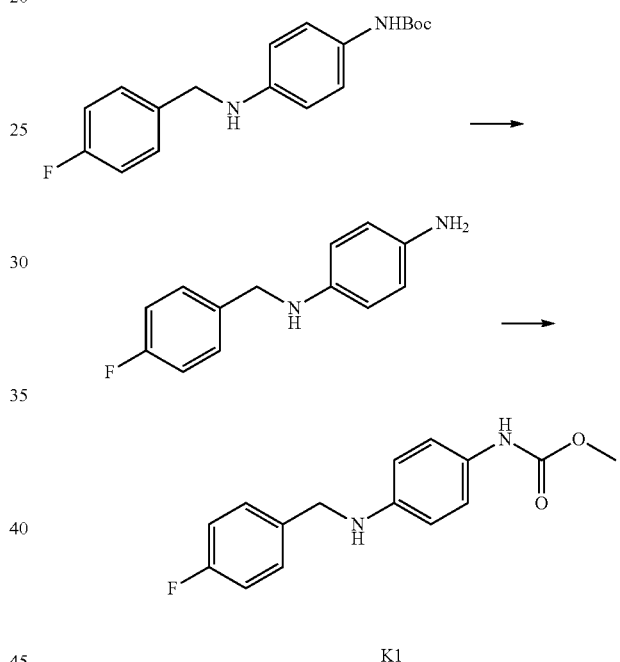

Mono-Boc-paraphenylenediamine (2.57 g, 0.0123 mol) and p-toluenesulfonic acid (62 mg, 0.32 mmol) were added in toluene (50 mL), parafluorobenzaldehyde (1.68 g, 0.0135 mol) was then added to obtain a mixture. The mixture was heated to azeotropy for 12 h so as to remove water thereto. Thereafter, the reaction solution was filtered while it was hot. A solid was precipitated when the filtrate was cooled down. The solid was filtered and dried, and the resulting crude product was obtained and was directly used for next step of reaction.

The above crude product (3.5 g, 11.1 mmol) was dissolved in a solution of dioxane/MeOH (30 mL, the volume ratio of dioxane/methanol is 4:1). NaBH$_4$ (697 mg, 0.018 mol) was then further added in batches with stirring at room temperature until the reaction was completed. After quenching with water, the reaction solution was extracted with EtOAc (15 mL×3). The organic phases were washed with saturated saline solution, dried with anhydrous Na$_2$SO$_4$ and concentrated, a product of tert-butyl 4-(N-parafluorobenzyl-imino)-aniline formate (3.5 g) was then obtained. $^1$H NMR (300 MHz, CDCl$_3$): δ 7.31 (t, J=8.4 Hz, 2H), 7.14 (d, J=8.4 Hz, 2H), 7.01 (t, J=8.7 Hz, 2H), 6.56 (d, J=9.0 Hz, 2H), 6.22 (s, 1H), 4.27 (s, 2H), 1.50 (s, 9H).

1.2. Synthesis of methyl 4-(N-parafluorobenzyl-imine)-aniline formate (K1)

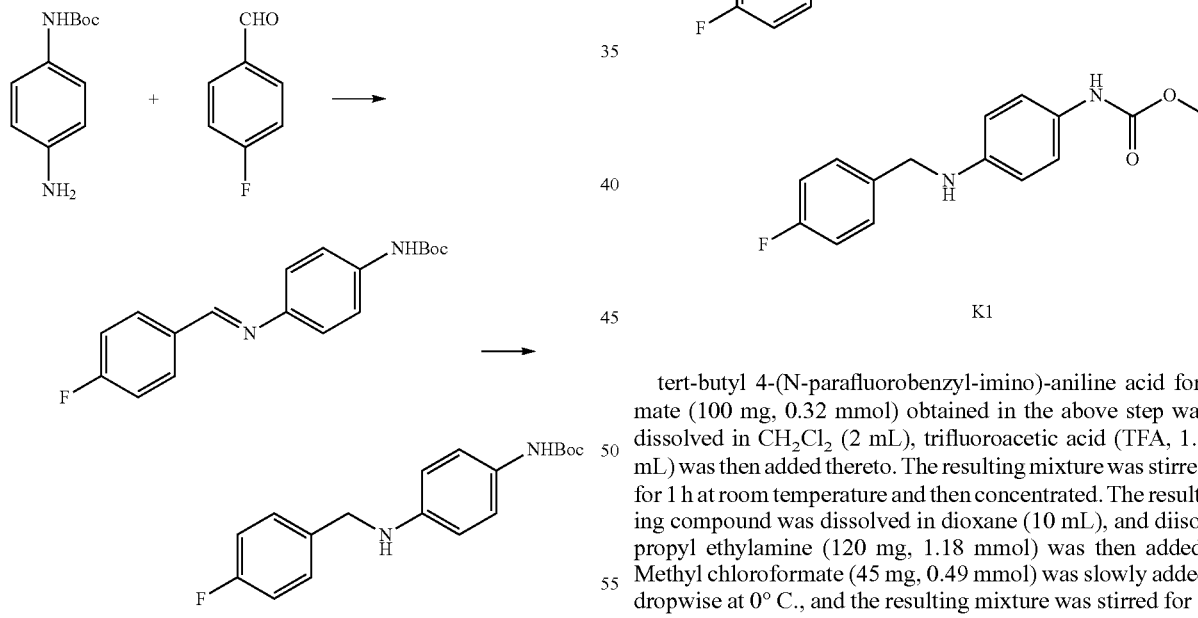

K1 tert-butyl 4-(N-parafluorobenzyl-imino)-aniline acid formate (100 mg, 0.32 mmol) obtained in the above step was dissolved in CH$_2$Cl$_2$ (2 mL), trifluoroacetic acid (TFA, 1.5 mL) was then added thereto. The resulting mixture was stirred for 1 h at room temperature and then concentrated. The resulting compound was dissolved in dioxane (10 mL), and diisopropyl ethylamine (120 mg, 1.18 mmol) was then added. Methyl chloroformate (45 mg, 0.49 mmol) was slowly added dropwise at 0° C., and the resulting mixture was stirred for 1 h at room temperature. Thereafter, the reaction solution was diluted with water and extracted with EtOAc (10 mL×3). The organic phases were washed with saturated saline solution, dried with anhydrous Na$_2$SO$_4$, concentrated and then loaded on chromatography column (PE/EtOAc=4:1). A product of methyl 4-(N-parafluorobenzyl-imine)-aniline formate (K1) was obtained. $^1$H NMR (300 MHz, CDCl$_3$): δ 7.13-7.26 (m, 4H), 6.87-6.96 (m, 4H), 6.61 (s, 1H), 4.26 (s, 2H), 3.77 (s, 3H).

Following compounds were obtained by using a procedure similar to that of Preparation example 1:

| Compound | Structural Formula | $^1$H NMR (CDCl$_3$, 300 MHz) data, δ |
|---|---|---|
| K2 | | 7.69(d, J = 7.8 Hz, 2H), 7.40-7.46(m, 6H), 7.24-7.34(m, 4H), 6.85-6.91(m, 4H), 6.61(s, 1H), 4.73(s, 2H), 4.38(s, 2H), 4.04-4.13(m, 1H), 1.52(s, 9H) |
| K3 | | 7.29(t, J = 8.4 Hz, 2H), 7.03(t, J = 8.4 Hz, 2H), 6.95(d, J = 6.6 Hz, 2H), 6.88(d, J = 6.9 Hz, 2H), 4.55(s, 2H), 4.03(s, 2H), 2.59(q, J = 7.2 Hz, 2H), 2.25(s, 1H), 1.10(t, J = 7.5 Hz, 3H) |

Preparation Example 2

Synthesis of methyl 4-(N-parafluorobenzyl-N-propargyl-imino)-aniline formate (K9)

2.1. Synthesis of tert-butyl 4-(N-parafluorobenzyl-N-propargyl-imino)-aniline formate

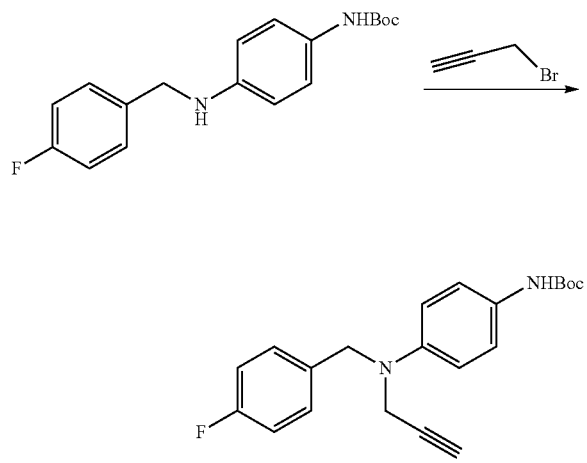

Compound tert-butyl 4-(N-parafluorobenzyl-imino)-aniline formate (316 mg, 1 mmol) was dissolved in DMF (N,N-dimethylformamide) (5 mL). Propargyl bromide (178 mg, 1.5 mmol) and diisopropyl ethylamine (i-Pr$_2$NEt) (258 mg, 2 mmol) were added dropwise. The resulting mixture was stirred for 2 h at 80° C., cooled, diluted with water and extracted with EtOAc (10 mL×3). The organic phases were washed with saturated saline solution, dried with anhydrous Na$_2$SO$_4$, concentrated and then loaded on chromatography column (the volume ratio of PE/EtOAc is 8:1). A product of tert-butyl 4-(N-parafluorobenzyl-N-propargyl-imino)-aniline formate (330 mg, 93.2%) was then obtained. $^1$H NMR (300 MHz, CDCl$_3$): δ 7.21-7.30 (m, 4H), 7.00 (t, J=8.4 Hz, 2H), 6.86 (d, J=9.0 Hz, 2H), 6.32 (s, 1H), 4.42 (s, 2H), 3.92 (d, J=2.4 Hz, 2H), 2.20 (t, J=2.4 Hz, 1H), 1.50 (s, 9H).

2.2. Synthesis of methyl 4-(N-parafluorobenzyl-N-propargyl-imino)-aniline formate

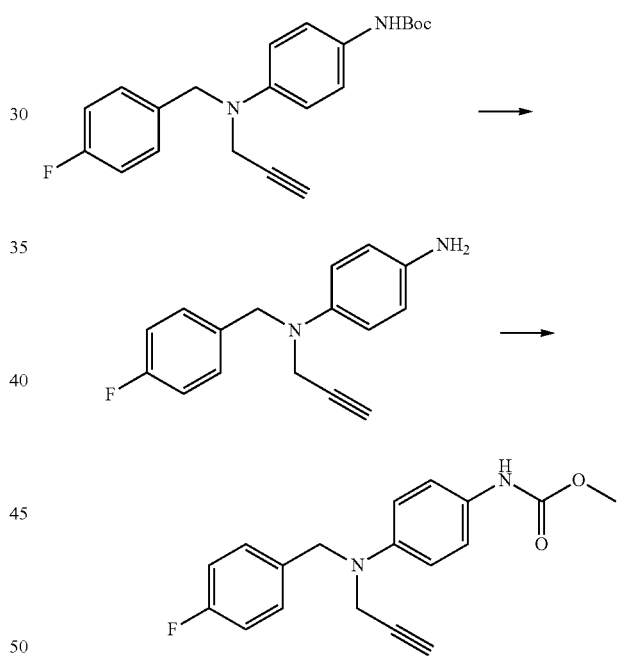

K9 tert-butyl 4-(N-parafluorobenzyl-N-propargyl-imino)-aniline formate (100 mg, 0.32 mmol) obtained in the above step was dissolved in CH$_2$Cl$_2$ (2 mL), trifluoroacetic acid (TFA, 1.5 mL) was then added thereto. The resulting mixture was stirred for 1 h at room temperature and then concentrated. The resulting compound was dissolved in dioxane (10 mL), and diisopropyl ethylamine (109 mg, 0.846 mmol) was then added. Methyl chloroformate (40 mg, 0.423 mmol) was slowly added dropwise at 0° C., and the resulting mixture was stirred for 1 h at room temperature. Thereafter, the reaction solution was diluted with water and extracted with EtOAc (10 mL×3). The organic phases were washed with saturated saline solution, dried with anhydrous Na$_2$SO$_4$, concentrated and then loaded on chromatography column (PE/EtOAc=4:1). A product of methyl 4-(N-parafluorobenzyl-N-propargyl-imino)-aniline formate (K9) was obtained. $^1$H NMR (300 MHz, CDCl$_3$): δ 7.23-7.28 (m, 4H), 6.99 (t, J=8.4 Hz, 2H), 6.83 (d, J=8.7 Hz, 2H), 4.41 (s, 2H), 3.91 (s, 2H), 3.72 (s, 3H), 2.22 (s, 1H).

Following compounds were obtained by using a procedure similar to that of Preparation example 2:

| Compound | Structural Formula | $^1$H NMR (CDCl$_3$, 300 MHz) data, δ |
|---|---|---|
| K4 | | 7.35-7.39(m, 4H), 7.25-7.30(m, 5H), 7.03(d, J = 8.7 Hz, 2H), 6.85(d, J = 8.7 Hz, 2H), 5.18(s, 2H), 4.44(s, 2H), 3.94(s, 2H), 2.22(s, 1H) |
| K5 | | 7.23-7.29(m, 4H), 6.99(t, J = 8.7 Hz, 2H), 6.83(d, J = 9.3 Hz, 2H), 6.67(s, 1H), 4.42(s, 2H), 3.93(s, 2H), 3.91(d, J = 4.2 Hz, 2H), 2.21(s, 1H), 1.92-1.97(m, 1H), 0.94(d, J = 6.6 Hz, 6H) |
| K6 | | 7.30(d, J = 8.7 Hz, 2H), 7.16(t, J = 8.7 Hz, 2H), 6.97(d, J = 8.4 Hz, 3H), 6.74(s, 1H), 4.76(s, 2H), 4.07-4.16(m, 4H), 1.64-1.68(m, 2H), 1.53-1.56(m, 2H), 1.33-1.35(m, 4H), 1.23-1.27(m, 4H), 0.91(t, J = 5.4 Hz, 3H), 0.84(t, J = 6.3 Hz, 3H) |
| K7 | | 7.15-7.23(m, 4H), 6.99(t, J = 8.7 Hz, 2H), 6.63(d, J = 9.0 Hz, 2H), 6.53(s, 1H), 5.80-5.89(m, 1H), 5.18(d, J = 1.5 Hz, 1H), 5.13(d, J = 3.3 Hz, 1H), 4.44(s, 2H), 4.18(q, J = 6.6 Hz, 2H), 3.93(d, J = 4.8 Hz, 2H), 1.26(t, J = 6.6 Hz, 3H) |
| K8 | | 7.23-7.29(m, 4H), 7.00(t, J = 8.4 Hz, 2H), 6.85(d, J = 9.0 Hz, 2H), 6.59(s, 1H), 4.42(s, 2H), 4.18(q, J = 7.2 Hz, 2H), 3.92(d, J = 2.1 Hz, 2H), 2.21(t, J = 2.4 Hz, 1H), 1.28(t, J = 7.2 Hz, 3H) |

Preparation Example 3

Synthesis of methyl 2-fluoro-5-(N-parafluorobenzyl-N-propargyl-imino)-aniline formate (K10)

3.1. Synthesis of methyl 2-fluoro-5-nitro aniline formate

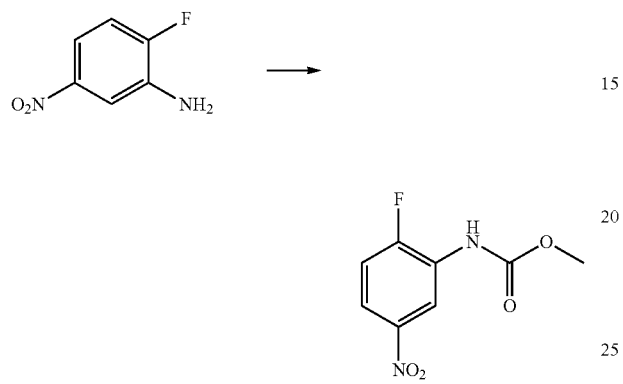

2-fluoro-3-nitro group aniline (156 mg, 1 mmol) was dissolved in dried THF (5 mL) under an atmosphere of nitrogen. The resulting solution was cooled to 0° C. in an ice-bath and sodium hydride (40 mg, 60%, 1 mmol) was added thereto. Then the solution was warmed to room temperature with stirring for 60 min. Thereafter, the solution was cooled to 0° C. and then methyl chloroformate (85.2 μL, 1.1 mmol) was added. After stirring for 10 min, the mixture was diluted with water (10 mL) and extracted with EtOAc (10 mL×3). The combined organic phases were washed with saturated saline solution (15 mL×3), dried with anhydrous $Na_2SO_4$, concentrated and then loaded on chromatography column (PE/EtOAc=10:1-5:1). A product of methyl 2-fluoro-5-nitro aniline formate (245 mg, 84.5%) was obtained.

3.2. Synthesis of methyl 2-fluoro-5-(N-parafluorobenzyl-N-propargyl-imino)-aniline formate (K10)

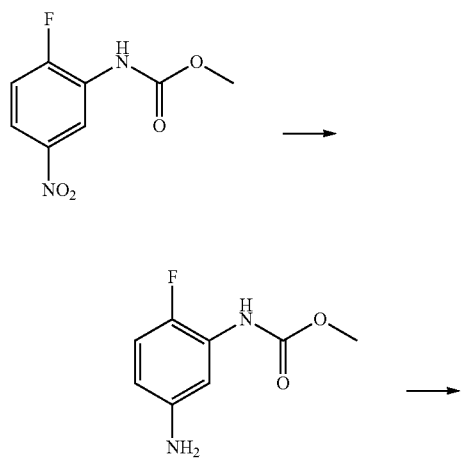

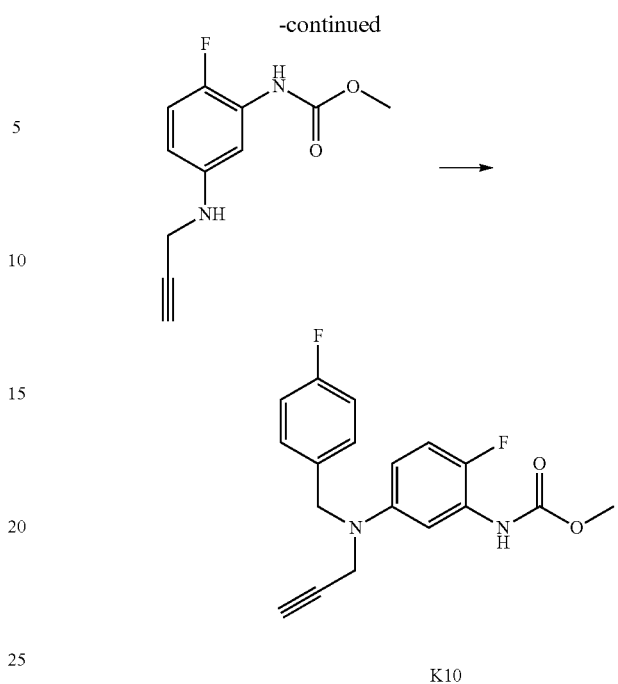

Compound methyl 2-fluoro-5-nitro aniline formate (95 mg, 0.443 mmol) obtained in the above step was dissolved in ethyl acetate (15 mL) and the air therein was replaced with $N_2$. Pd—C (10%, 5 mg) was rapidly added in the obtained solution and $N_2$ therein was replaced with $H_2$. The resulting solution was kept at room temperature for 6 h, filtered and concentrated to produce a compound of methyl 2-fluoro-5-aminoaniline formate (72.5 mg, 89.1%) in the form of colorless oil, which was directly used in the nest step;

under an atmosphere of nitrogen, compound methyl 2-fluoro-5-aminoaniline formate (72.5 mg, 0.39 mmol) was dissolved in dried DMF (5 mL), then propargyl bromide (44 μL, 0.59 mmol) and DIPEA (140 μL, 0.78 mmol) were added. The resulting solution was stirred for 6 h at 60° C., and diluted with water (10 mL) and extracted with EtOAc (10 mL×3). The combined organic phases were washed with saturated saline solution (15 mL×3), dried with anhydrous $Na_2SO_4$, concentrated and then loaded on chromatography column (PE/EtOAc=6:1-4:1) to produce a product of methyl 2-fluoro-5-(N-propargyl-imino)-aniline formate (70.1 mg, 81%);

under an atmosphere of nitrogen, methyl 2-fluoro-5-(N-propargyl-imino)-aniline formate (70 mg, 0.32 mmol) was dissolved in dried DMF (5 mL), then 4-fluorobenzyl bromide (81 μL, 0.64 mmol) and diisopropyl ethylamine (DIPEA) (115 μL, 0.64 mmol) were added. The resulting solution was stirred for 6 h at 60° C., was diluted with water (10 mL) and extracted with EtOAc (10 mL×3). The combined organic phases were washed with saturated saline solution (15 mL×3), dried with anhydrous $Na_2SO_4$, concentrated and then loaded on chromatography column (PE/EtOAc=6:1-4:1) to produce a product of methyl 2-fluoro-5-(N-parafluorobenzyl-N-propargyl-imino)-aniline formate (K10) (88.7 mg, 84%). $^1H$ NMR (300 MHz, $CDCl_3$): δ 7.79 (s, 1H), 7.30 (m, 2H), 7.01 (m, 2H), 6.93 (dd, J=9.9 Hz, J=9.0 Hz, 2H), 6.83 (s, 1H), 6.51 (m, 1H), 7.01 (m, 2H), 4.44 (s, 2H), 3.94 (d, J=2.4 Hz, 2H), 3.79 (s, 3H), 2.24 (t, J=2.4 Hz, 1H).

Following compounds were obtained by using a procedure similar to that of Preparation example 3:

| Compound | Structural Formula | ¹H NMR (CDCl₃, 300 MHz) data, δ |
|---|---|---|
| K11 | (structure) | 7.80 (s, 1H), 7.59 (d, J = 6.6 Hz, 1H), 7.55 (m, 1H), 7.15 (t, J = 8.1 Hz, 2H), 6.95 (dd, J = 9.0 Hz, J = 10.5 Hz, 2H), 6.84 (S, 1H), 6.48 (m, 1H), 4.48 (s, 2H), 3.97 (d, J = 2.4 Hz, 2H), 3.78 (s, 3H), 2.27 (t, J= 2.1 Hz, 1H) |
| K12 | (structure) | 7.31 (t, J = 8.7 Hz, J = 5.7 Hz, 1H), 7.25 (m, 2H), 7.10 (d, J = 7.2 Hz, 2H), 7.04 (d, J = 9.9 Hz, 1H), 6.95 (td, J = 8.4 Hz, J = 2.1 Hz, 1H), 6.81 (d, J = 10.8 Hz, 2H), 6.57 (s, 1H), 4.48 (s, 2H), 3.98 (d, J = 2.1 Hz, 2H), 3.75 (s, 3H) |
| K13 | (structure) | 7.32 (t, J = 8.7 Hz, J = 7.5 Hz, 1H), 7.24 (m, 3H), 7.10 (d, J = 7.2 Hz, 1H), 7.06 (d, J= 9.9 Hz, 1H), 6.80 (d, J = 5.7 Hz, 2H), 6.64 (s, 1H), 4.56 (s, 2H), 4.10 (d, J = 2.4Hz, 2H), 3.75 (s, 3H), 2.25 (t, J = 2.4, 1H) |
| K14 | (structure) | 8.08 (d, J = 8.1 Hz, 1H), 7.78 (s, 1H), 7.56 (d, J = 6.6 Hz, 1H), 7.44 (m, 1H), 7.36 (dd, J = 6.6 Hz, J = 1.2 Hz, 1H), 7.19 (t, J = 7.5 Hz, 1H), 7.12 (t, J = 9.0 Hz, 1H), 7.01 (td, J = 7.5 Hz, J = 1.5 Hz, 1H), 4.16 (s, 2H), 3.78 (s, 3H), 3.59 (d, J = 2.1 Hz, 2H), 2.36 (t, J = 2.1 Hz, 1H) |
| K15 | (structure) | 7.80 (brs, 1H), 7.55 (d, J = 6.3 Hz, 1H), 7.49 (m, 1H), 7.17 ( t, J = 9.6 Hz, 1H), 6.64-6.59 (m, 2H), 6.53 (s, 1H), 4.49 (s, 2H), J = 3.97 (d, J = 2.7 Hz, 2H), 3.77 (s, 3H), 2.26 (t, J = 2.7 Hz,1H) |

-continued

| Compound | Structural Formula | ¹H NMR (CDCl₃, 300 MHz) data, δ |
|---|---|---|
| K16 | | 7.37-7.29(m, 2H), 7.25(d, J = 8.4 Hz, 2H), 7.06-6.93(m, 4H), 6.43(brs, 1H), 4.90(m, 1H), 3.78(d, J = 2.4 Hz, 2H), 3.75(s, 2H), 2.16(t, J = 2.4 Hz, 1H), 1.54-1.47(m, 3H) |
| K17 | | 7.41-7.30(m, 2H), 7.25-7.19(m, 4H), 6.46(brs, 1H), 4.59(s, 2H), 4.06(d, J = 2.4 Hz, 2H), 3.75(s, 3H), 2.25(t, J = 2.4 Hz, 1H) |
| K18 | | 7.26-7.22(m, 4H), 6.90-6.85(m, 4H), 6.48(d, J = 8.4 Hz, 2H), 6.43(brs, 1H), 4.42(s, 2H), 3.93(d, J = 2.1 Hz, 2H), 3.80(s, 3H), 3.75(s, 3H), 2.21(t, J = 2.4 Hz, 1H) |
| K19 | | 7.26(d, J = 8.7 Hz, 2H), 7.18-7.05(m, 3H), 6.85(d, J = 8.7 Hz, 1H), 6.47(brs, 1H), 4.42(s, 2H), 3.96(d, J = 2.1 Hz, 2H), 3.69(s, 3H), 2.23(t, J = 2.4Hz, 1H) |

Preparation Example 4

Synthesis of ethyl 2-amino-4-(N-parafluorobenzyl-N-allyl-imino)-aniline formate (K20)

4.1. Synthesis of tert-butyl 2-(tert-butoxycarbonyl imino)-4-(N-parafluorobenzyl-imino)-aniline formate

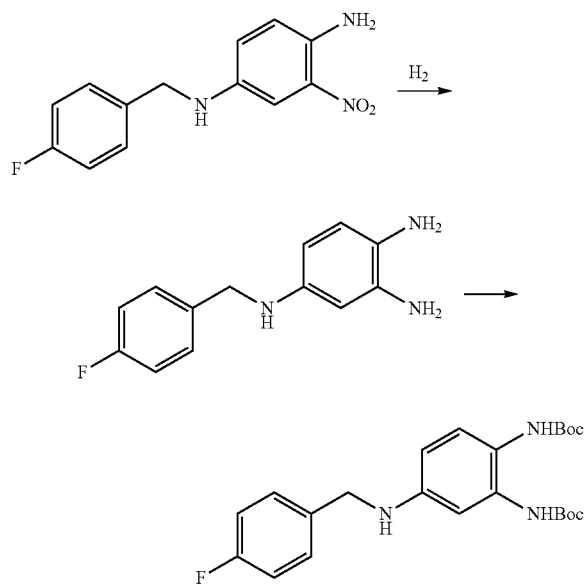 [SMILES: Nc1ccc(NCc2ccc(F)cc2)cc1[N+](=O)[O-] ; "H2" ; Nc1ccc(NCc2ccc(F)cc2)cc1N ; CC(C)(C)OC(=O)Nc1ccc(NCc2ccc(F)cc2)cc1NC(=O)OC(C)(C)C]

According to a procedure similar to that of Preparation example 1, intermediate 2-nitro-4-(N-parafluorobenzyl-imino)-aniline was obtained by using o-nitro paraphenylene diamine and parafluorobenzaldehyde as starting materials. 2-nitro-4-(N-parafluorobenzyl-imino)-aniline (2.61 g, 0.01 mol) was dissolved in THF (30 mL) and air therein was replace with $N_2$. Then Pd—C (10%, 261 mg) was rapidly added and $N_2$ therein was replaced with $H_2$. The hydrogenation reaction was conducted overnight, and the resulting reaction solution was filtered and concentrated to produce a product of 2-amino-4-(N-parafluorobenzyl-imino)-aniline (2.3 g, 99.6%, colorless oil, instable, prone to be oxidized and deteriorated), which was rapidly used in nest step. $^1$H NMR (300 MHz, CDCl$_3$): δ 7.32 (t, J=8.7 Hz, 2H), 7.02 (t, J=8.7 Hz, 2H), 6.58 (d, J=8.7 Hz, 1H), 6.01-6.08 (m, 2H), 4.22 (s, 2H).

2-amino-4-(N-parafluorobenzyl-imino)-aniline (1 g, 4.32 mmol) obtained in the above step was dissolved in THF/H$_2$O (40 mL, 1:1), di-tert-butoxy carbonic anhydride (Boc$_2$O) (2.83 g, 12.96 mmol) and sodium bicarbonate (1.16 g, 12.96 mmol) were added thereto. The resulting solution was stirred overnight at room temperature, diluted with water, and extracted with EtOAc (30 mL×3). The combined organic phases were washed with saturated saline solution (15 mL×3), dried with anhydrous Na$_2$SO$_4$. The pooled organic phase was concentrated under reduced pressure to remove solvent, and the residue was purified by silica gel chromatography column (PE/EtOAc=5:1) to produce an intermediate tert-butyl 2-(tert-butoxycarbonyl imino)-4-(N-parafluorobenzyl-imino)-aniline formate (1.67 g, 89.5%, colorless oil). $^1$H NMR (300 MHz, CDCl$_3$): δ 7.28 (t, J=8.7 Hz, 2H), 7.00 (t, J=8.7 Hz, 3H), 6.89 (s, 1H), 6.26 (d, J=8.7 Hz, 1H), 4.25 (s, 2H), 1.48 (s, 18H).

4.2. Synthesis of tert-butyl 2-(tert-butoxycarbonyl imino)-4-(N-parafluorobenzyl-N-allyl-imino)-aniline formate

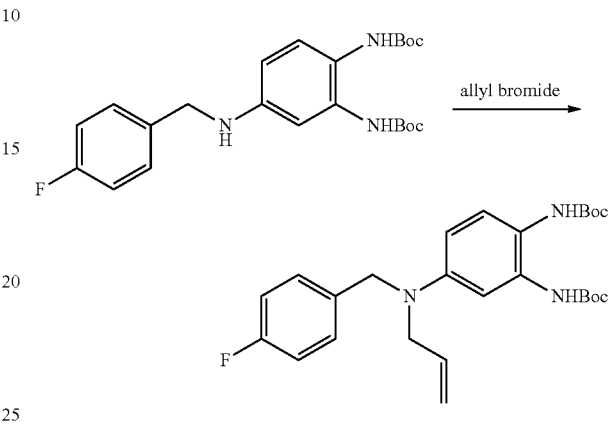

Intermediate tert-butyl 2-(tert-butoxycarbonyl imino)-4-(N-parafluorobenzyl-imino)-aniline formate (150 mg, 0.348 mmol) was dissolved in DMF (5 mL). Allyl bromide (55 mg, 0.452 mmol) and i-Pr$_2$NEt (99 mg, 0.766 mmol) were added dropwise. The resulting solution was stirred for 2 h at 50° C., and then was cooled down, diluted with water (10 mL) and extracted with EtOAc (10 mL×3). The organic phases were washed with saturated saline solution, dried with anhydrous Na$_2$SO$_4$, concentrated and then loaded on chromatography column (PE/EtOAc=4:1) to produce a compound of tert-butyl 2-(tert-butoxycarbonyl imino)-4-(N-parafluorobenzyl-N-allyl-imino)-aniline formate (143 mg, 87.2%, colorless oil). $^1$H NMR (300 MHz, CDCl$_3$): δ 7.18 (t, J=6.9 Hz, 2H), 6.90-7.06 (m, 4H), 6.49 (s, 1H), 6.48 (d, J=8.7 Hz, 1H), 5.79-5.88 (m, 1H), 5.18 (s, 1H), 5.13 (s, 1H), 4.44 (s, 2H), 3.92 (d, J=3.6 Hz, 2H), 1.49 (s, 18H). $^{13}$C NMR (75 MHz, CDCl$_3$): δ 163.5, 160.3, 154.9, 153.5, 147.5, 134.4, 134.3, 133.4, 128.4, 128.3, 127.0, 116.7, 115.5, 115.2, 80.4, 53.4, 53.1, 28.3.

4.3. Synthesis of ethyl 2-amino-4-(N-parafluorobenzyl-N-allyl-imino)-aniline formate (K20)

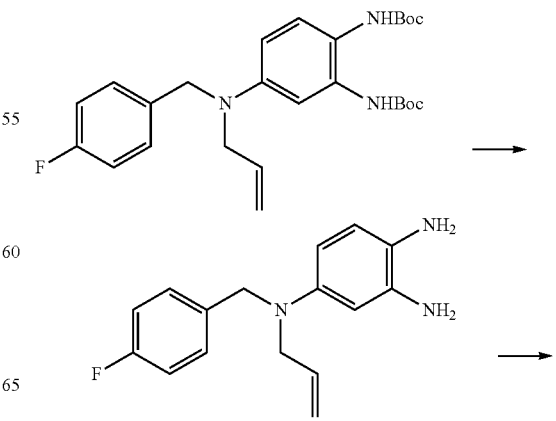

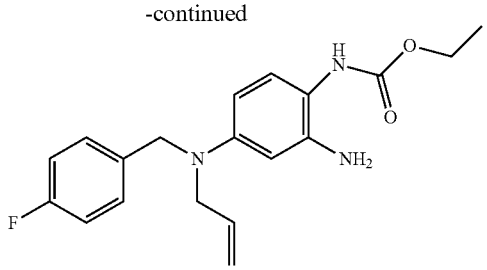

K20

Compound tert-butyl 2-(tert-butoxycarbonyl imino)-4-(N-parafluorobenzyl-N-allyl-imino)-aniline formate (80 mg, 0.17 mmol) was dissolved in $CH_2Cl_2$ (0.2 mL), and TFA (1 mL) was further added thereto. The resulting solution was stirred for 1 h at room temperature and concentrated. The residue was dissolved in dioxane (10 mL), DIPEA (66 mg, 0.51 mmol) was added and a solution of ethyl chloroformate (18 mg, 0.17 mmol) in dioxane (2 mL) was slowly added dropwise at 0° C. The resulting solution was stirred at room temperature for 1 h, and then diluted with water and extracted with EtOAc (10 mL×3). The organic phases were washed with saturated saline solution, dried with anhydrous $Na_2SO_4$, concentrated and then loaded on chromatography column (PE/EtOAc=4:1-2:1) to produce a product of ethyl 2-amino-4-(N-parafluorobenzyl-N-allyl-imino)-aniline formate (K20) (28 mg, colorless oil). $^1$HNMR (300 MHz, $CDCl_3$): δ 7.18 (t, J=8.1 Hz, 2H), 6.99 (t, J=8.4 Hz, 1H), 6.91 (d, J=8.7 Hz, 1H), 6.12 (d, J=8.7 Hz, 2H), 6.06 (d, J=2.1 Hz, 1H), 5.80-5.86 (m, 1H), 5.19 (s, 1H), 5.14 (d, J=3.0 Hz, 1H), 4.44 (s, 2H), 4.20 (q, J=6.9 Hz, 2H), 3.91 (d, J=4.5 Hz, 2H), 3.59 (brs, 2H), 1.28 (t, J=6.9 Hz, 3H).

Following compounds were obtained by using a procedure similar to that of Preparation example 4:

| Compound | Structural Formula | $^1$H NMR ($CDCl_3$, 300 MHz) data, δ |
|---|---|---|
| K21 | | 7.25(t, J = 8.1 Hz, 2H), 6.99(t, J = 8.7 Hz, 2H), 6.26-6.31(m, 3H), 4.44(s, 2H), 4.17(q, J = 7.2 Hz, 2H), 3.93(s, 2H), 2.22(s, 1H), 1.27(t, J = 7.2Hz, 3H) |
| K29 | | 7.16(dd, J = 7.5 Hz, J = 5.7 Hz, 2H), 7.06(d, J = 8.7 Hz, 1H), 6.98(t, J = 8.4 Hz, 2H), 6.91(brs, 1H), 6.74(s, 1H), 6.37(s, 1H), 6.37(d, J = 8.7 Hz, 2H), 4.87(s, 1H), 4.80(s, 1H), 4.49(s, 2H), 3.83(s, 2H), 1.72(s, 3H), 1.48(s, 18H) |
| K33 | | 7.25(t, J = 8.4 Hz, 2H), 7.15(s, 1H), 7.01(t, J = 8.7 Hz, 2H), 6.40(d, J = 8.4 Hz, 2H), 4.46(s, 2H), 4.29(t, J = 4.5 Hz, 2H), 3.96(s, 2H), 3.67(s, 8H), 3.80(t, J = 9.0 Hz, 2H), 2.23(s, 1H) |

Preparation Example 5

Synthesis of methyl 2-(methoxy carbonyl-imino)-4-(N-parafluoro benzyl-N-propargyl-imino)-aniline formate (K22)

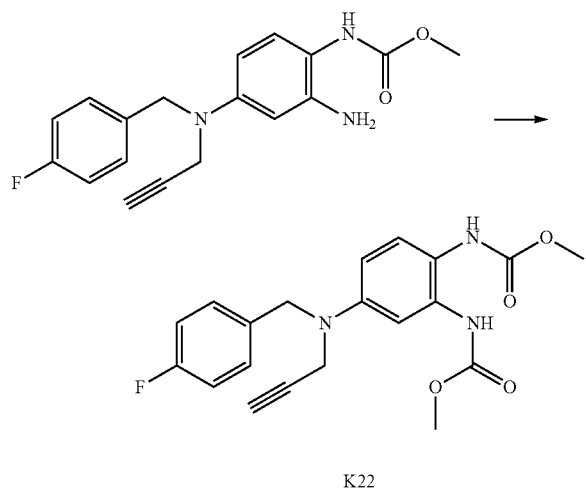

Compound methyl 2-amino-4-(N-parafluorobenzyl-N-propargyl-imino)-aniline formate was obtained by using a procedure similar to that of Preparation example 4. The resulting compound (80 mg, 0.24 mmol) was dissolved in dioxane (10 mL), DIPEA (100 mg, 0.98 mmol) was further added thereto, and a solution of methyl chloroformate (50 mg, 0.53 mmol) in dioxane (2 mL) was slowly added dropwise at 0° C. The mixture was stirred at the room temperature until the reaction was completed. The resulting solution was diluted with water and extracted with EtOAc (10 mL×3). The organic phases were washed with saturated saline solution, dried with anhydrous $Na_2SO_4$, concentrated and then loaded on chromatography column (PE/EtOAc=4:1-2:1) to produce a product of methyl 2-(methoxy carbonyl-imino)-4-(N-parafluorobenzyl-N-propargyl-imino)-aniline formate (K22) (68 mg, 72%). $^1$H NMR (300 MHz, $CDCl_3$): δ 7.25 (t, J=8.4 Hz, 2H), 7.12 (d, J=8.7 Hz, 2H), 6.99 (t, J=8.7 Hz, 2H), 6.57 (d, J=8.7 Hz, 1H), 4.45 (s, 2H), 3.94 (s, 2H), 3.71 (s, 6H), 2.22 (s, 1H).

Following compounds were obtained by using a procedure similar to that of Preparation example 5:

| Compound | Structural Formula | $^1$H NMR ($CDCl_3$, 300 MHz) data, δ |
|---|---|---|
| K23 | | 7.25(t, J = 8.4 Hz, 2H), 7.09-7.15(m, 2H), 7.01(t, J = 8.7 Hz, 2H), 6.59(d, J = 6.0 Hz, 1H), 4.47(s, 2H), 4.20(q, J = 6.3 Hz, 4H), 3.91(s, 2H), 1.79(s, 3H), 1.28(t, J = 7.2 Hz, 6H) |
| K24 | | 7.26(t, J = 9.0 Hz, 2H), 7.15(d, J = 8.4 Hz, 2H), 7.03(t, J = 8.7 Hz, 2H), 6.60(d, J = 8.7 Hz, 1H), 4.49(s, 2H), 4.20(q, J = 6.9 Hz, 4H), 3.95(s, 2H), 2.17(q, J = 5.7 Hz, 2H), 1.29(t, J = 6.9 Hz, 6H), 1.10(t, J = 7.5 Hz, 3H) |
| K26 | | 7.14 (dd, J = 8.7 Hz, J = 5.4 Hz, 2H), 7.07 (d, J = 9.0 Hz, 1H), 7.00 (t, J = 8.4 Hz, 2H), 6.41 (brs, 1H), 6.41 (dd, J = 8.7 Hz, J = 2.4, 2H), 4.47 (s, 2H), 4.19 (m, 4H), 3.35 (t, J = 7.2 Hz, 2H), 2.47 (t, J = 6.9 Hz, 2H), 2.11 (s, 3H), 1.90 (m, 2H), 1.29 (t, J = 6.9 Hz, 6H). |

-continued

| Compound | Structural Formula | ¹H NMR (CDCl₃, 300 MHz) data, δ |
|---|---|---|
| K27 | | 7.17 (dd, J = 8.4 Hz, J = 5.4 Hz, 4H), 7.03 (d, J = 9.0 Hz, 1H), 6.97 (t, J = 9.0 Hz, 4H), 6.72 (brs, 2H) 6.35 (dd, J = 9.0 Hz, J = 2.7 Hz, 2H), 4.50 (s, 4H), 4.22 (t, J = 6.9 Hz, 4H), 4.13 (t, J = 7.2 Hz, 4H), 3.99 (s, 4H), 1.67 (s, 6H), 1.28 (m, 12H) |
| K28 | | 7.21 (dd, J = 8.7 Hz, J = 5.7 Hz, 2H), 7.09 (d, J = 9.0 Hz, 1H), 7.03 (t, J = 8.7 Hz, 2H), 6.41 (s, 1H), 6.41 (d, J = 8.7, 2H), 4.92 (s, 1H), 4.85 (s, 1H), 3.88 (s, 2H), 3.78 (s, 3H), 3.77 (s, 3H), 1.77 (s, 3H) |
| K30 | | 7.17 (dd, J = 8.7 Hz, J = 5.4 Hz, 2H), 7.06 (d, J = 9.0 Hz, 1H), 6.99 (t, J = 8.7 Hz, 2H), 6.86 (s, 1H), 6.38 (s, 1H), 6.38 (dd, J = 8.7 Hz, J = 2.4 Hz, 2H), 4.97 (m, J = 6.3 Hz, 2H), 4.88 (s, 1H), 4.81 (s, 1H), 4.50 (s, 2H), 3.84 (s, 2H), 561.73 (s, 3H), 1.27 (m, ) |
| K31 | | 7.19 (dd, J = 8.4 Hz, J = 5.7 Hz, 2H), 7.06 (d, J = 8.4 Hz, 2H), 6.96 (t, J = 8.4 Hz, 3H), 6.42 (s, 1H), 6.42 (dd, J = 8.7 Hz, J = 2.4 Hz, 2H), 5.23 (t, J = 6.3 Hz, 2H), 4.43 (s, 2H), 3.91 (d, J = 6.3 Hz, 2H), 3.74 (s, 3H), 3.73 (s, 3H), 1.71 (s, 3H), 1.63 (s, 3H) |
| K35 | | 7.34-7.26 (m, 4H), 7.19-7.14 (dd, J = 8.4 Hz, J = 8.1 Hz, 4H), 7.07 (d, J = 8.7 Hz, 1H), 6.98 (t, J = 8.7 Hz, 4H), 6.54 (s, 1H), 6.44 (d, J = 7.5 Hz, 1H), 5.44 (s, 1H), 5.16 (s, 1H), 4.55 (s, 2H), 4.29 (s, 2H), 4.19 (m, 4H), 1.28 (t, J = 7.2 Hz, 6H) |

| Compound | Structural Formula | $^1$H NMR (CDCl$_3$, 300 MHz) data, δ |
|---|---|---|
| K36 | 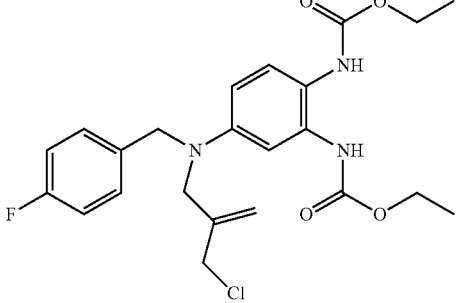 | 7.17 (dd, J = 8.4 Hz, J = 5.4 Hz, 2H), 7.08 (d, J = 9.0 Hz, 2H), 6.99 (t, J = 9.0 Hz, 2H), 6.94 (s, 1H), 6.44 (dd, J = 9.0 Hz, J = 2.7 Hz, 1H), 6.44 (brs, 1H), 5.29 (s, 1H), 5.11 (s, 1H), 4.54 (s, 2H), 4.18 (m, 4H), 4.07 (s, 2H), 1.28 (m, 6H) |
| K37 | 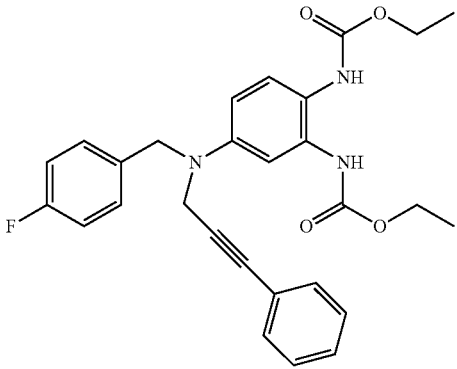 [SMILES: CCOC(=O)Nc1ccc(N(CC#Cc2ccccc2)Cc2ccc(F)cc2)cc1NC(=O)OCC] | 7.39-7.37 (m, 2H), 7.34-7.26 (m, 5H), 7.18 (d, J = 8.7 Hz, 1H), 7.02 (t, J = 8.7 Hz, 2H), 6.66 (dd, J = 8.7 Hz, J = 2.1 Hz, 1H), 6.52 (brs, 1H), 4.56 (s, 2H), 4.20 (m, 6H), 1.29 (m, 6H) |
| K38 | 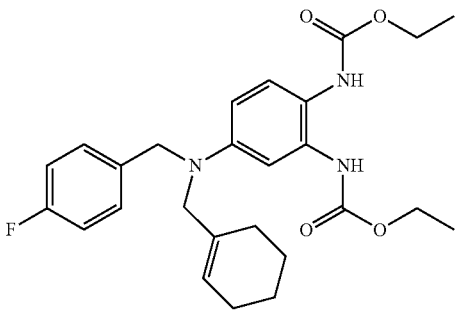 [SMILES: CCOC(=O)Nc1ccc(N(CC2=CCCCC2)Cc2ccc(F)cc2)cc1NC(=O)OCC] | 7.16 (dd, J = 8.4 Hz, J = 5.4 Hz, 2H), 7.05 (d, J = 8.7 Hz, 1H), 6.98 (t, J = 9.0 Hz, 4H), 6.88 (brs, 2H) 6.39 (dd, J = 9.0 Hz, J = 2.7 Hz, 2H), 5.50 (s, 1H), 4.47 (s, 4H), 4.20 (m, 4H), 3.80 (s, 2H), 2.04 (m, 2H) 1.99 (m, 2H) 1.60 (m, 4H), 1.28 (m, 6H) |

Preparation Example 6

Synthesis of 5-(N-parafluorobenzyl-N-propargyl-imino)-benzimidazole-2-one (K25)

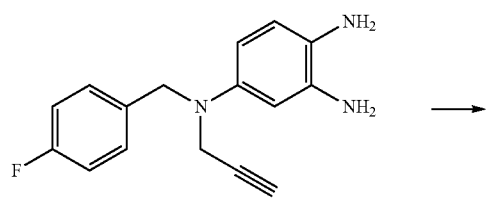

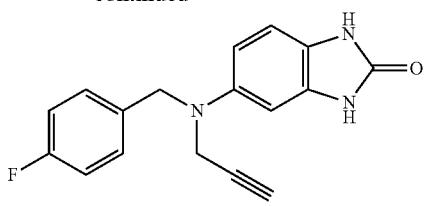

K25

2-amino-4-(N-parafluorobenzyl-N-propargyl-imino)-aniline was obtained by using method of Preparation example 4. The resulting compound (27 mg, 0.1 mmol) was dissolved in THF (5 mL). A solution of solid Triphogene (30 mg, 0.1 mmol) in THF (2 mL) and Et₃N (30 mg, 0.3 mmol) were added dropwise thereto. The resulting solution was stirred for 2 h at room temperature for 2 h, and concentrated and loaded on column (PE/EtOAc/MeOH=10:10:1-5:5:1) to produce a product of 5-(N-parafluorobenzyl-N-propargyl-imino)-benzimidazole-2-one (K25) (25 mg, 84.5%). $^1$H NMR (300 MHz, CD$_3$OD): δ 7.34 (t, J=8.7 Hz, 2H), 7.03 (t, J=8.7 Hz, 2H), 6.89 (d, J=8.7 Hz, 1H), 6.72 (d, J=8.7 Hz, 2H), 4.42 (s, 2H), 3.95 (s, 2H), 2.60 (s, 1H).

Compound 5-(N-parafluorobenzyl-N-allyl-imino)-benzimidazole-2-one (K34) was obtained by using a method similar to that of Preparation example 6. $^1$H NMR (300 MHz, DMSO-d$_6$); δ 10.22 (s, 1H), 10.14 (s, 1H), 7.26 (t, J=7.8 Hz, 2H), 7.13 (d, J=8.1 Hz, 1H), 6.69 (d, J=8.4 Hz, 1H), 6.32 (d, J=8.4 Hz, 1H), 6.28 (s, 1H).

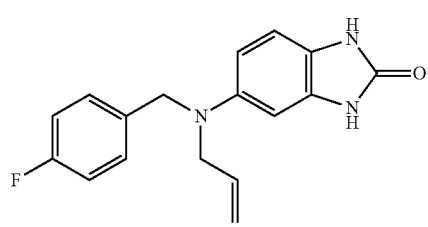

K34

Preparation Example 7

Synthesis of ethyl 2-(ethoxy carbonyl-imino)-4-[N-parafluorobenzyl-N-1-(6-hydroxyl-2-alkenyl-3-hexylene)-imino]-aniline formate (K32)

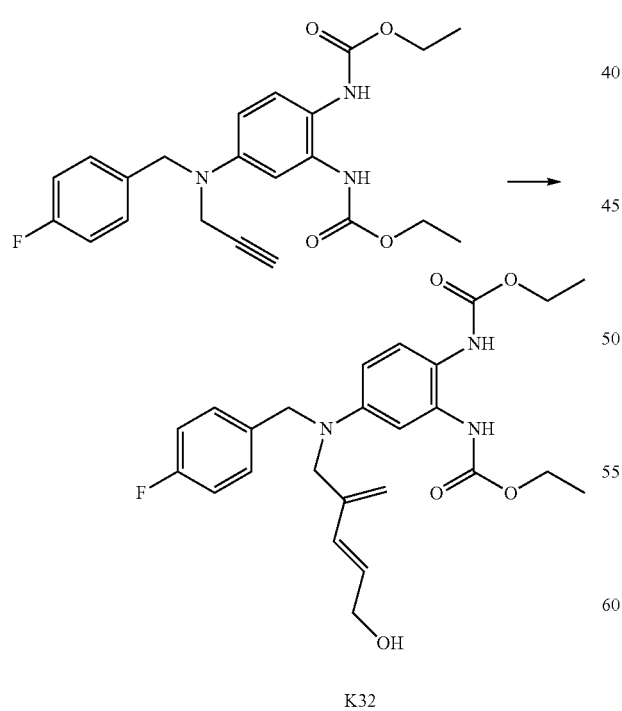

K32

Compound ethyl 2-(ethoxy carbonyl-imino)-4-(N-parafluorobenzyl-N-propargyl-imino)-aniline formate was obtained by using a method similar to that of Preparation example 5. Under an atmosphere of argon, the resulting compound (15 mg, 0.036 mmol) and allyl alcohol (21 mg, 0.36 mmol) were dissolved in anhydrous dichloromethane (3 ml), and oxygen therein was removed by insufflation of argon for 15 min. Grubbs II catalyst was rapidly added, in, the atmosphere was changed for 3 times and the resulting reaction mixture was reflux overnight. The reaction mixture was concentrated at reduced pressure to remove solvent, and the residue was purified on silica gel chromatography column (PE/EtOAc=4:1-2:1) to produce a product of ethyl 2-(ethoxy carbonyl-imino)-4-[N-parafluorobenzyl-N-1-(6-hydroxyl-2-alkenyl-3-hexylene)-imino]-aniline formate K32 (15 mg, 85%) in a form of black oil. $^1$H NMR (300 MHz, CDCl$_3$): δ 7.18 (dd, J=8.7 Hz, J=8.4 Hz, 2H), 7.07-6.96 (m, 5H), 6.40 (dd, J=8.7 Hz, J=2.7 Hz, 1H), 6.36 (s, 1H), 5.88-5.79 (dt, J=16.2 Hz, J=5.15 Hz, 1H), 5.03 (s, 1H), 4.52 (s, 1H), 4.18 (m, 4H), 4.10 (s, 2H), 1.28 (m, 6H).

Compound ethyl 2-(ethoxycarbonyl-imino)-4-[N-parafluorobenzyl-N-1-(6-amino-2-alkenyl-3-hexylene)-imino]-aniline formate (K39) was obtained by using a method similar to that of Preparation example 7. $^1$H NMR (CDCl$_3$, 300 MHz); δ 7.17 (dd, J=8.4 Hz, J=5.4 Hz, 2H), 7.07 (d, J=9.0 Hz, 2H), 6.98 (t, J=8.7 Hz, 2H), 6.59 (s, 1H), 6.35 (dd, J=9.0 Hz, J=2.7 Hz, 1H), 6.29 (d, J=15.9 Hz, 1H), 5.76 (d,j=15.9 Hz, 1H), 5.11 (s, 1H), 4.99 (s, 1H), 4.49 (s, 2H), 4.17 (m, 4H), 4.08 (s, 2H), 1.25 (m, 6H).

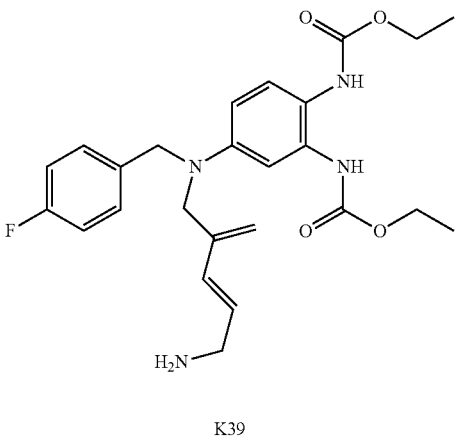 [SMILES: C=C(/C=C/CN)CN(Cc1ccc(F)cc1)c1ccc(NC(=O)OCC)c(NC(=O)OCC)c1 ; "K39"]

K39

Preparation Example 8

Preparation of ethyl 2-amino-4-(N-parafluorobenzyl-N-propargyl-imino)-aniline formate dihydrochloride (K21.2HCl)

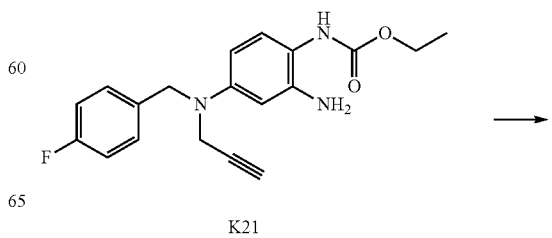

K21

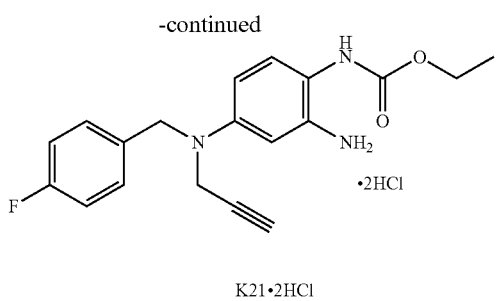

K21·2HCl 511 mg (1.5 mmol) of compound ethyl 2-amino-4-(N-parafluorobenzyl-N-propargyl-imino)-aniline formate (K21) was dissolved in dichloromethane (5 mL). A solution (1 mL) of HCl (5N) in ethyl acetate was added, the resulting solution was stirred for 10 min and the solvent was removed under reduced pressure, thereby obtaining a compound of ethyl 2-amino-4-(N-parafluorobenzyl-N-propargyl-imino)-aniline formate dihydrochloride (K21.2HCl) (624 mg).

The hydrochlorides of compound K3 (K3.HCl), compound K17 (K17.HCl) and compound K18 (K18.HCl) as well as dihydrochloride of compound K20 (K20.2HCl) were obtained by using a method similar to that of Preparation example 8.

II. Electrophysiological Experiment Example

Electrophysiological Experiment of the Present Compounds on Chinese Hamster Oocytes (CHO)

1. Cell Culture and Transfection

The formulation of culture fluid for Chinese hamster oocytes (CHO) (Culture Collection of Chinese Academy of Sciences): 50/50 DMEM/F-12 (Cellgro, Mamassas, Va.), 10% fetal bovine serum (FBS) (Gibco, Australia) and 2 mM L-glutamic acid (Invitrogen). Expression and mutation of KCNQ channels: 24 h before transfection, oocytes were lysed with trypsin (Sigma, China) and plated on a culture dish with diameter of 60 mm. Lipofectamine2000™ agent (Invitrogen) was used for Transfection according to the protocol thereof. 24 h after the transfection, cells were lysed and replated on slides immersed with poly-L-lysine (Sigma). After cotransfection with GFP (green fluorescent protein), transfected cells could be determined under a fluorescence microscopy.

2. Electrophysiological Recordings in CHO Cells

Whole-cell voltage-clamp recording was performed by using Axopatch-200B amplifier (Molecular Devices, Sunnyvale, Calif.) at room temperature. Borosilicate glass capillary tubes (World Precision Instruments, Sarasota, Fla.) were drawn into electrodes. The electric resistance of the electrodes filled with an intracellular fluid is 3 to 5 MΩ. The formulation of the intracellular fluid was as follows: 145 mM KCl, 1 mM $MgCl_2$, 5 mM EGTA, 10 mM HEPES and 5 mM MgATP (the pH value of the intracellular fluid was adjusted to 7.3 with KOH). During the recording, an extracellular fluid was continuously perfused by using a BPS perfusion system (ALA Scientific Instruments, Westburg, N.Y.). The formulation of the extracellular fluid was as follows: 140 mM NaCl, 5 mM KCl, 2 mM $CaCl_2$, 1.5 mM $MgCl_2$, 10 mM HEPES and 10 mM glucose (the pH value of the extracellular fluid was adjusted to 7.4 with NaOH). Electric signal was filtered at 1 kHz and further converted into digital signal by using pClamp 9.2 software (Molecular Devices, Sunnyvale, Calif.) in Digi-Data 1322A. Resistors were connected in series to compensate 60 to 80% of signal loss. At present, multivoltage scheme was generally adopted, wherein the clamp voltage was set at −100 mV. Current was induced in cells by a series of 2000 ms stimulating voltage (from −90 mV up to +50 mV, with interval of 10 mV).

3. Experimental Results

In the following table, $V_{1/2}$ is the voltage at which 50% of cells were activated, $\Delta V_{1/2}$ is amount of a left-ward shift of $V_{1/2}$, negative sign (−) represents a left-ward shift of the current activation curve and positive sign (+) represents a right-ward shift of the curve. $I/I_0$ is the activation multiple, wherein, $I_0$ is the maximum induced current produced under stimulation of −10 mV testing voltage, I is the maximum induced current produced under stimulation of −10 mV testing voltage after administration (10 μM), $I/I_0>1$ represents activating activity, and $I/I_0<1$ represents inhibiting activity. N is the number of tested cells. NT represents non-tested.

| Compound | $\Delta V_{1/2}$ (mV) | $I/I_0$ | N |
| --- | --- | --- | --- |
| K1 | −8.1 ± 3.1 | 2.84 ± 0.08 | 3 |
| K2 | −3.0 ± 2.0 | 1.50 ± 0.08 | 4 |
| K3•HCl | −13.9 ± 2.5 | 2.41 ± 0.20 | 3 |
| K4 | −11.5 ± 2.0 | 2.09 ± 0.25 | 3 |
| K5 | −14.3 ± 3.3 | 1.23 ± 0.08 | 4 |
| K6 | −1.6 ± 3.0 | 1.24 ± 0.02 | 3 |
| K7 | −4.7 ± 2.0 | 1.35 ± 0.27 | 2 |
| K8 | −7.3 ± 2.5 | 1.99 ± 0.37 | 3 |
| K9 | −24.21 ± 2.4 | 3.27 ± 0.10 | 3 |
| K10 | −18.7 ± 2.6 | 2.75 ± 0.31 | 3 |
| K11 | −15.7 ± 1.0 | 2.24 ± 0.36 | 3 |
| K12 | −21.1 ± 1.9 | 2.33 ± 0.17 | 3 |
| K13 | −7.6 ± 1.9 | 2.31 ± 0.36 | 3 |
| K14 | −14.7 ± 2.1 | 1.43 ± 0.04 | 4 |
| K15 | −22.0 ± 1.5 | 2.09 ± 0.31 | 3 |
| K16 | −20.6 ± 4.5 | 1.47 ± 0.10 | 3 |
| K17•HCl | −16.5 ± 2.4 | 2.29 ± 0.38 | 3 |
| K18•HCl | −12.5 ± 3.2 | 2.72 ± 0.22 | 3 |
| K19 | −14.9 ± 2.7 | 2.52 ± 0.23 | 3 |
| K20 | −49.7 ± 3.4 | 1.75 ± 0.12 | 3 |
| K21 | −47.9 ± 3.5 | 1.53 ± 0.15 | 3 |
| K22 | −27.31 ± 3.9 | 2.10 ± 0.35 | 3 |
| K23 | −15.34 ± 3.8 | 1.44 ± 0.14 | 3 |
| K24 | −1.87 ± 2.5 | 1.2 ± 0.1 | 3 |
| K25 | −5.8 ± 1.7 | 1.8 ± 0.1 | 3 |
| K26 | NT | 1.25 ± 0.07 | 3 |
| K27 | NT | 1.52 ± 0.17 | 3 |
| K28 | NT | 1.43 ± 0.05 | 3 |
| K29 | NT | 1.24 ± 0.10 | 3 |
| K30 | NT | 1.57 ± 0.25 | 3 |
| K31 | NT | 1.36 ± 0.13 | 3 |
| K32 | −6.0 ± 1.5 | 1.76 ± 0.09 | 3 |
| K33 | −36.8 ± 3.3 | NT | 3 |
| K34 | NT | 1.44 ± 0.16 | 3 |
| K35 | NT | NT | |
| K36 | NT | NT | |
| K37 | NT | NT | |
| K38 | NT | 0.16 ± 0.02 | 3 |
| K39 | NT | 1.03 ± 0.11 | 3 |

III. Examples for Evaluation on Pharmacodynamics Effects of Compounds In Vivo

In Vivo Pharmacodynamics Effects Example 1

Therapeutic Effects of Compounds K9 and K1 on Convulsion Induced by Pentylenetetrazole (PTZ)

1. Object of Experiment

Comparison of the anti-convulsive effects of compounds K9 and K1 with that of retigabine (prepared in the lab according to procedure disclosed in U.S. Pat. No. 5,384,330).

2. Treatment of Samples

Retigabine: in the form of light grey powder, it can be easily dissolved in water to produce a colorless and transparent solution.

Compound K9: in the form of yellow granule, it can not be easily dissolved in water. The compound was added into a solution of 0.2% CMC, and ultrasonic treatment was performed for 30 min, thereby obtaining a homogeneous suspension.

Compound K1: in the form of light yellow granule, it can not be easily dissolved in water. The compound was added into a solution of 0.2% CMC, and ultrasonic treatment was performed for 30 min, thereby obtaining a homogeneous suspension.

3. Laboratory Animals

C57BL/6J mice (body weight: 16 g to 18 g) were purchased from Laboratory Animal Center, Chinese Academy of Sciences.

4. Experimental Procedure

The compounds to be tested were administered to animals by gastric lavage (30 mg/kg); one hour later, pentylenetetrazole was administered by subcutaneous injection (PTZ 80 mg/kg); and response of animals were observed within a period of 60 min.

5. Experimental Results:

1. Object of Experiments

The anti-convulsive effect of compound K21 was compared with that of retigabine as a positive control.

2. Treatment of Samples

Retigabine: in the form of light grey powder, it can be easily dissolved in water to produce a colorless and transparent solution.

Compound K21: in the form of cyan lamellar granule, it can not be easily dissolved in water. The compound was dissolved in 50 ul of DMSO, and 0.5% of HEC was added to produce a homogeneous suspension.

3. Laboratory Animals

KM mice (male, body weight: 22±2 g) were purchased from Laboratory Animal Center, Chinese Academy of Sciences.

4. Experimental Procedure (1) Test with PTZ

Compounds to be tested were administrated by intraperitoneal injection (10 mg/kg, 5 mg/kg, 2.5 mg/kg, 0.1 ml/10 g). 30 min later, pentylenetetrazole (PTZ, 100 mg/kg) was administered by subcutaneous injection. Response of animals were observed immediately and recorded within a period of 1 h.

(2) Test with MES

YLS-9A model physiological pharmaceutical electronic stimulator was used with configuration 8, and the stimulating voltage was set as 160V, wave number as 90, i.e., the period of

| Compound | Dosage, Administration route, period of observation | Number | Incidence rate of convulsion | Latency period of clonus (s) | Latency period of whole-body tonic seizures(s) | Mortality rate |
|---|---|---|---|---|---|---|
| K9 | 1 h after | 10 | 4/10 | 351 ± 84.3 | 1382 ± 339 | 4/10 |
| K1 | administration | 10 | 4/10 | 250 ± 114 | 1785 ± 408 | 3/10 |
| Retigabine | by gastric lavage (30 mg/kg) | 10 | 5/10 | No typical clonic seizures were observed | 1472 ± 961 | 4/10 |
| Control of PTZ | | 10 | 9/10 | 134 ± 51.5 | 921 ± 248 | 8/10 |

Animals treated with retigabine were quite and less active. After 20 min, animals returned to normal. After 1 h, no significant abnormal response was observed. For the animals treated with compounds K9 and K1 respectively, the convulsion incidence rates decreased significantly, which were manifested by for prolonged latency period of clonic seizures in mice with acute convulsion induced by PTZ, prolonged latency period of whole-body tonic seizures, and reduced mortality. The above results indicated that compounds of K9, K11 and retigabine had a comparable anti-convulsive effect.

In Vivo Pharmacodynamics Effect Example 2: Therapeutic Effects of Compounds K21 Administrated by Intraperitoneal Injection on Animal Models Induced by PTZ (Pentylenetetrazole) and MES (Maximum Electroshock)

stimulation was 5.4 sec. One time of electrical stimulation was applied to animals through ear clip electrodes, and a convulsion characterized by a tonic hind limb extension was observed. One day before the test, animals were screened in the above procedure to record the values of MES. On test, the compounds to be tested were administered to animals by intraperitoneal injection (10 mg/kg, 0.1 ml/10 g), and 30 min later, MES was applied according to parameters set the last day, and response of animals were observed and recorded immediately.

5. Experimental Results:

(1) Results of PTZ Test

| Compound | Dosage | Administration route, period of observation | Incidence rate of convulsion | Latency period of clonus (s) | Incidence of tonic fore limb extension | Incidence of tonic hind limb extension | Latency period of tonic hind limb(sec) | Mortality rate |
|---|---|---|---|---|---|---|---|---|
| K21 | 10 mg/kg | Intraperitoneal | 12/12 | 226 ± 51** | | 0/12*** | | 0/12*** |
| K21 | 5 mg/kg | injection, | 10/10 | 238 ± 54*** | 3/10 | 0/10*** | | 1/10** |
| K21 | 2.5 mg/kg | observation for | 9/10 | 184 ± 42 | 2/10 | 0/10*** | | 1/10** |
| Retigabine | 10 mg/kg | 1 h | 10/10 | 239 ± 113** | | 4/12* | 1100 ± 319 | 2/12** |
| Retigabine | 5 mg/kg | | 10/10 | 184 ± 40 | 4/10 | 2/10* | 883 ± 151 | 5/10 |
| Retigabine | 2.5 mg/kg | | 10/10 | 179 ± 60 | 5/10 | 1/10** | 827 | 7/10 |

-continued

| Compound | Dosage | Administration route, period of observation | Incidence rate of convulsion | Latency period of clonus (s) | Incidence of tonic fore limb extension | Incidence of tonic hind limb extension | Latency period of tonic hind limb(sec) | Mortality rate |
|---|---|---|---|---|---|---|---|---|
| Physiological saline | 0.2 ml | | 11/11 | 137 ± 24 | 3/11 | 8/11 | 1033 ± 364 | 9/11 |

*p < 0.05,
**p < 0.01,
***p < 0.001

(2) Results of MES Test

| Compound | Dosage, administration route | Incidence of convulsion | Mortality rate |
|---|---|---|---|
| K21 | 10 mg/kg, administration by intraperitoneal injection | 2/10*** | 0 |
| Retigabine | | 4/11** | 0 |
| Physiological saline | | 10/10 | 10% |

*p < 0.05,
**p < 0.01,
***p < 0.001

6. Experimental Conclusion

Compound K21 completely avoided the grand mal seizure in MES test, significantly reduced the incidence rate of convulsion and mortality rate in PTZ test, and prolonged the latency period of clonic seizures in mice with acute convulsion with a dose-response relationship to a certain degree. At the same dosage, the anti-convulsive effect of compound K21 was slightly stronger than that of retigabine as a positive control, and both of them exhibited some sedative effect.

In Vivo Pharmacodynamics Effect Example 3: Therapeutic Effects of Compounds K21 Orally Administered on Animal Models Induced by PTZ and MES 3. Laboratory Animals KM mice (male, body weight: 22±2 g for PTZ test; 18 g for MES test) were purchased from Laboratory Animal Center, Chinese Academy of Sciences.

4. Experimental Procedure (1) Test with PTZ

Animals were fasted for 12 h, and then compounds CF341 and retigabine (30 mg/kg, 0.2 ml/10 g) were administrated by gastric lavage. 1 h later, pentylenetetrazole (PTZ, 100 mg/kg) was administered by subcutaneous injection. Response of animals were observed immediately and recorded within a period of 1 h.

(2) Test with MES

YLS-9A model physiological pharmaceutical electronic stimulator was used with configuration 8, and the stimulating voltage was set as 160V, wave number as 90, i.e., the period of stimulation was 5.4 sec. One time of electrical stimulation was applied to animals through ear clip electrodes, and a convulsion characterized by a tonic hind limb extension was observed. One day before the test, animals were screened in the above procedure to record the values of MES.

Animals were fasted for 12 h, the compounds to be tested (30 mg/kg, 0.2 ml/10 g) were then administrated by gastric lavage. 1 hour later, MES was applied according to parameters set the last day, and response of animals were observed and recorded immediately.

5. Experimental Results (1) Results of PTZ Test

| Compound | Dosage | Administration route, period of observation | Incidence rate of clonus | Latency period of clonus(sec) | Incidence of tonic fore limb extension | Incidence of tonic hind limb extension | Latency period of fore limb extension (sec) | Mortality rate |
|---|---|---|---|---|---|---|---|---|
| K21 | 30 mg/kg | Administrated by gastric lavage, observation for 1 h | 12/12 | 148 ± 37* | 5/12 | 0/12** | 1561 ± 690 | 3/12 |
| Retigabine | 30 mg/kg | | 12/12 | 177 ± 70 | 3/12** | 0/12** | 1063 ± 284 | 0/12** |
| Physiological saline | 0.4 ml | | 12/12 | 104 ± 18 | 9/12 | 7/12 | 964 ± 174 | 7/12 |

When compared with negative control,
*represents p < 0.05 and
**represents p < 0.01.

1. Object of Experiments

The anti-convulsive effect of compound K21 orally administrated was compared with that of retigabine as an positive control.

2. Treatment of Samples

Retigabine: in the form of light grey powder, it can be easily dissolved in water to produce a colorless and transparent solution.

Compound K21: in the form of cyan lamellar granule, it can not be easily dissolved in water. The compound was dissolved in 50 ul of DMSO, the resulting solution added into 0.2% of CMC solution, and ultrasonic treatment was performed for 20 min to produce a homogeneous suspension.

(2) Results of MES Test

| Compound | Dosage, administration route | Incidence rate of convulsion | Protection rate of compounds |
|---|---|---|---|
| K21 | 30 mg/kg, administered by gastric lavage | 2/13*** | 84.6%*** |
| retigabine | | 5/13*** | 61.5%*** |
| NS | | 13/13 | 0% |

When compared with negative control,
***represents p < 0.001.

7. Experimental Conclusion

Both compound K21 and retigabine exhibited similar effect in significantly inhibiting the incidence of the grand mal seizure in MES test. In PTZ test, retigabine could obviously reduce the incidence rate of convulsion and mortality rate of animals. Compound K21 could significantly inhibit tonic seizures of animals, although the mortality rate of K21 group is less than that of control, there was no significant differences between them.

IV. Pharmacokinetics Examples of Compounds

Pharmacokinetics Example 1

Research on Distribution of K9 and Retigabine in Mice's Brain Tissue

1. Dosage Regimen

Before test, 108 of healthy KM mice (male, body weight: 18 g to 20 g) were fasted for 12 h with access to water ad libitum. Two hours after administration, animal were fed uniformly. Specific arrangement was as following table.

| Group | number of animals | Compound | Administration manner | Administration dosage (mg/kg) | Administration volume (ml/kg) | Sampling time point(h) |
|---|---|---|---|---|---|---|
| 1 | 27 | K9 | Gastric lavage | 20 | 10 | 0.25, 0.5, 1, 2, 3, 4, 6, 8 and 10 h |
| 2 | 27 | K9 | Intravenous injection | 20 | 10 | 5 min, 0.25, 0.5, 1, 2, 4, 6, 8 and 10 h |
| 3 | 27 | retigabine | Gastric lavage | 20 | 10 | 0.25, 0.5, 1, 2, 3, 4, 6, 8 and 10 h |
| 4 | 27 | retigabine | Intravenous injection | 20 | 10 | 5 min, 0.25, 0.5, 1, 2, 4, 6, 8 and 10 h |

Before test, animals were fasted for 12 h with access to water ad libitum. Two hours after administration, animal were fed uniformly.

After administration by gastric lavage or intravenous injection, mice were sacrificed by cutting abdominal aorta at time points set as the above with 3 mice for each time point. 0.5 mL of whole blood was collected for each animal, placed into a heparinized test tube and subjected to centrifugation at 3000 rpm to separate plasma, which was then cryopreserved in a −20° C. refrigerator. After the animals were sacrificed, their whole brain was collected, washed with ice-cooled physiological saline to remove residual blood. Then the residual liquid was absorbed to dryness. The treated brain was labeled and cryopreserved in a −20° C. refrigerator.

2. Experimental Results

The concentrations of K9 and retigabine in plasma and brain tissue were determined by LC-MS.

2.1. K9

After mice were administrated with compound K9 (20 mg/kg) by gastric lavage, the maximum concentrations ($C_{max}$) in plasma and brain tissue were 2197 ng/ml and 4421 ng/g respectively. The corresponding areas under the concentration-time curve ($AUC_{0-t}$) were 1865 ng·h/ml and 3565 ng·h/g respectively. The exposure amount in brain tissue was 1.9 times of that in plasma. The elimination half-life of K9 was about 1.2 h.

After mice were administrated with compound K9 (20 mg/kg) by intravenous injection, the corresponding areas under the concentration-time curve ($AUC_{0-t}$) of plasma and brain tissue were 7185 ng·h/ml and 10694 ng·h/g respectively. Plasma clearance rate was 2.78 L/h/kg. The exposure amount in brain of compound K9 was 1.5 times of that in plasma.

Upon dose correction, the absolute bioavailability following administration with compound $K_9$ by gastric lavage (20 mg/kg) in mice was 26% according to $AUC_{0-t}$ of plasma.

2.2 Retigabine

After mice were administrated with retigabine (20 mg/kg) by gastric lavage, the maximum concentrations ($C_{max}$) in plasma and brain tissue were 2788 ng/ml and 849 ng/g respectively. The corresponding areas under the concentration-time curve ($AUC_{0-t}$) were 21088 ng·h/ml and 3460 ng·h/g respectively. The exposure amount in brain tissue was 16% of that in plasma. The elimination half-life of retigabine was about 7 h.

After mice were administrated with retigabine (20 mg/kg) by intravenous injection, the corresponding areas under the concentration-time curve ($AUC_{0-t}$) of plasma and brain tissue were 59987 ng·h/ml and 8661 ng·h/g respectively. Plasma clearance rate was 0.322 L/h/kg. The exposure amount in brain of retigabine was 14% of that in plasma.

Upon dose correction, the absolute bioavailability following administration with retigabine by gastric lavage (20 mg/kg) in mice was 35.2% according to $AUC_{0-t}$ of plasma.

Pharmacokinetics Example 2

Research on Distribution of K20.2HCl and K21.2HCl in Mice's Brain Tissue

1. Dosage Regimen

Before test, 54 healthy KM mice (male, body weight: 18 g to 20 g) were fasted for 12 h with access to water ad libitum. Two hours after administration, animal were fed uniformly. Specific arrangement was as following table.

| Group | number of animals | Compound | Administration manner | Administration dosage (mg/kg) | Administration volume (ml/kg) | Sampling time point(h) |
|---|---|---|---|---|---|---|
| 1 | 27 | K20•2HCl | gastric lavage | 20 | 10 | 0.25, 0.5, 1, 2, 3, 5, 7, 9 and 24 h |
| 2 | 27 | K21•2HCl | gastric lavage | 5* | 10 | 0.25, 0.5, 1, 2, 3, 5, 7, 9 and 24 h |

As for "*", mice administrated with compounds K21•2HCl by gastric lavage (20 mg/kg) were obviously restless, and one of them died, therefore, the administration dosage was decreased to 5 mg/kg.

Before test, animals were fasted for 12 h with access to water ad libitum. Two hours after administration, animal were fed uniformly.

After administration by gastric lavage, mice were sacrificed by cutting abdominal aorta at time points set as the above with 3 mice for each time point. 0.5 mL of whole blood was collected for each animal, placed into a heparinized test tube and subjected to centrifugation at 11000 rpm for 10 min to separate plasma, which was then cryopreserved in a −20° C. refrigerator. After the animals were sacrificed, their whole brain was dissected and collected, washed with ice-cooled physiological saline to remove residual blood. Then the residual liquid was absorbed to dryness. The treated brain was labeled and cryopreserved in a −20° C. refrigerator.

2. Experimental Results 2.1. K20.2HCl

After mice were administrated with compound K20.2HCl (20 mg/kg) by gastric lavage, time to reach the maximum concentrations ($T_{max}$) for prototype drug K20.2HCl and its metabolite retigabine in plasma or brain tissue was 0.25 h. The exposure amounts of metabolite retigabine in plasma and brain tissue were 2.9% and 1.8% of those of prototype drug K20.2HCl, respectively. The concentration of prototype drug K20.2HCl in brain tissue was 2.3 times of that in plasma, and for metabolite retigabine, 1.4 times.

2.2, K21.2HCl

After mice were administrated with compound K21.2HCl (5 mg/kg) by gastric lavage, time to reach the maximum concentrations ($T_{max}$) for prototype drugs K21.2HCl and its metabolite retigabine in plasma or brain tissue was 0.25 h. The exposure amounts of metabolite retigabine in plasma and brain tissue were 5.4% and 4.6% of those of prototype drug K21.2HCl, respectively. The concentration of prototype drug K21.2HCl in brain tissue was 2.4 times of that in plasma, and for metabolite retigabine, 2.0 times.

As can be seen from the above experimental results, the compounds provided by the present invention not only maintain retigabine's activating activities on potassium ion channels, but also exhibit a significant anti-epilepsy effect in vivo.

1. In male KM mice model, compound K21.2HC administrated by intraperitoneal injection exhibits superior anti-convulsive effect to that of compound retigabine as a positive control.

2. Similarly, in male KM mice model, compound K21.2HC and retigabine administrated by gastric lavage (10 mg/kg) show comparable effect in MES test, in other words, both of them can significantly prevent grand mal seizures. In PTZ test, retigabine can significantly reduce the incidence rate of convulsion and mortality rate of animals, while compound K21.2HCl can obviously inhibit the tonic seizures of animals.

Pharmacokinetics research showed that the compounds of the present invention have better concentration distribution in brain tissue, compared with retigabine.

1. After mice are administrated with compound K9 by gastric lavage (20 mg/kg), the exposure amount thereof in brain tissue is 1.9 times of that in plasma. After mice are administrated with compound K9 by intravenous injection (20 mg/kg), the exposure amount thereof in brain is 1.5 times of that in plasma. Under the same condition, as for retigabine administrated by gastric lavage and intravenous injection, the exposure amounts in brain are 16% and 14% of those in plasma.

2. After mice are administrated with compound K20 by gastric lavage (20 mg/kg), the concentration thereof in brain tissue is 2.3 times of that in plasma.

3. After mice are administrated with compound K21.2HCl by gastric lavage (5 mg/kg), the concentration thereof in brain tissue is 2.4 times of that in plasma.

The invention claimed is:

1. A compound or the pharmaceutically acceptable salt having a structure of general formula III:

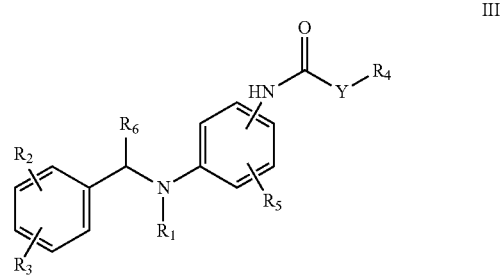

wherein, $R_1$ is a radical selected from the group consisting of $C_2$-$C_8$ alkenyl, $C_5$-$C_7$ cycloalkenyl and $C_2$-$C_8$ alkynyl; wherein, the $C_2$-$C_8$ alkenyl is unsubstituted or optionally substituted by hydroxyl, amino, halogen atom, phenyl or halogenated phenyl; the $C_2$-$C_8$ alkynyl is unsubstituted or optionally substituted by hydroxyl, amino, halogen atom, phenyl or halogenated phenyl;

$R_2$ is a radical selected from the group consisting of F, Cl and methoxyl;

$R_3$ is a radical selected from the group consisting of H, halogen atom and trifluoromethyl;

Y is not present or Y is O;

$R_4$ is a radical selected from the group consisting of $C_1$-$C_6$ alkyl, $C_2$-$C_6$ alkenyl, $C_2$-$C_6$ alkynyl and $C_6$-$C_{10}$ aryl;

$R_5$ is a radical selected from the group consisting of H, halogen atom, amino and

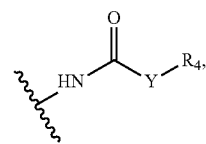

or R₅, together with adjacent
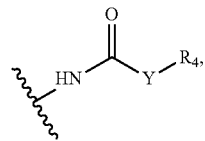
forms a fused-ring structure of
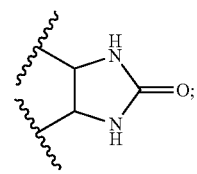 [SMILES: *C1NC(=O)NC1*]
R₆ is H or $C_1$-$C_6$ alkyl.
2. The compound or the pharmaceutically acceptable salt thereof according to claim 1, wherein the compound is one selected from the group consisting of:
K4
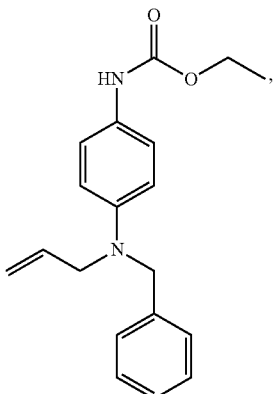
K5
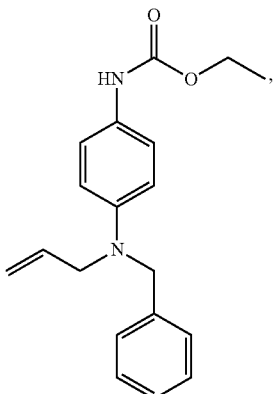
-continued
K7
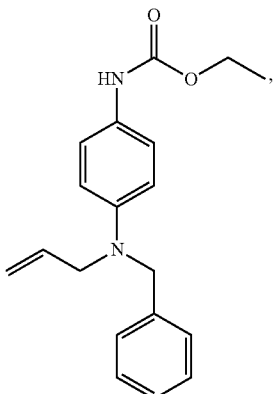
K8
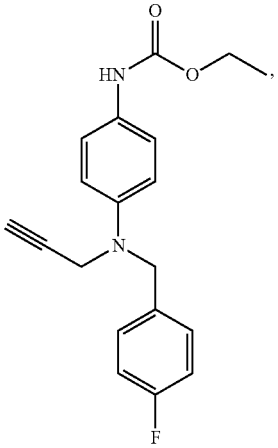
K9
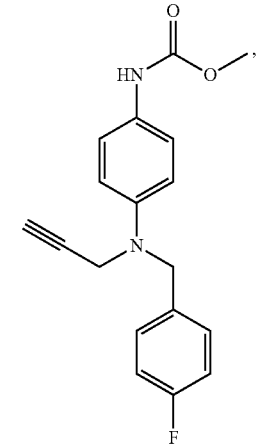
K10
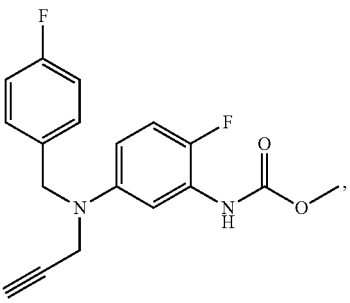

K11
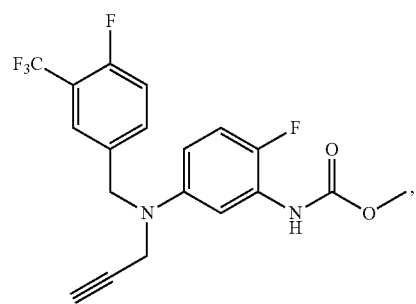
K12
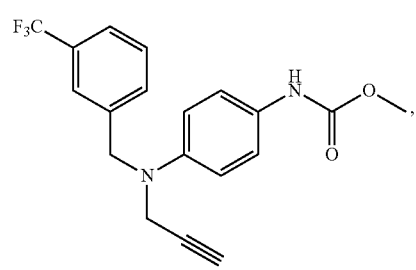
K13
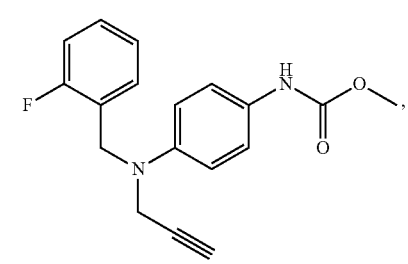
K14
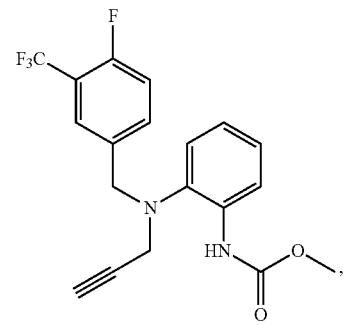
K15
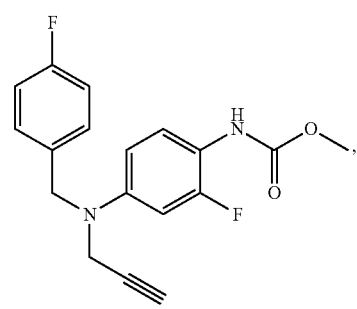
K16
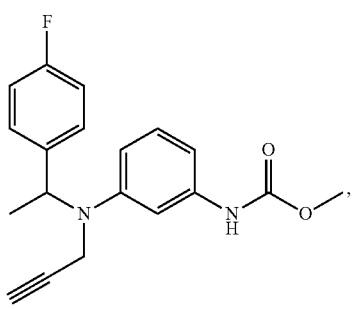
K17
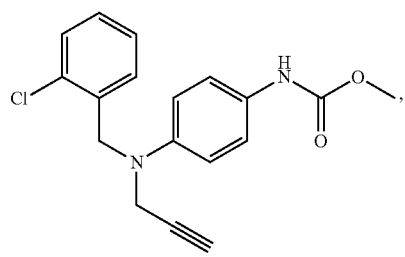
K18
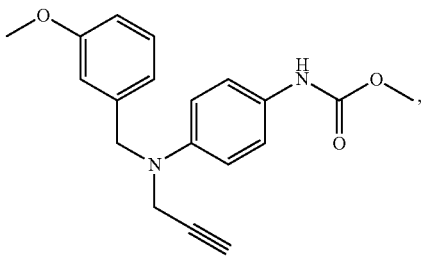
K19
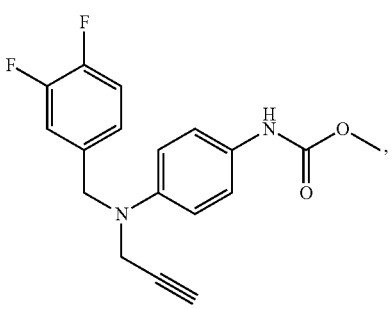
K20
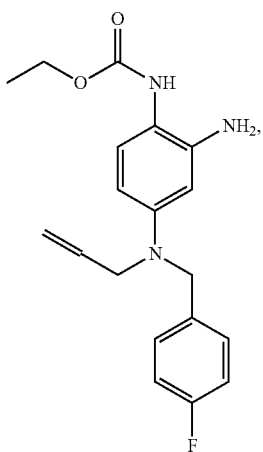

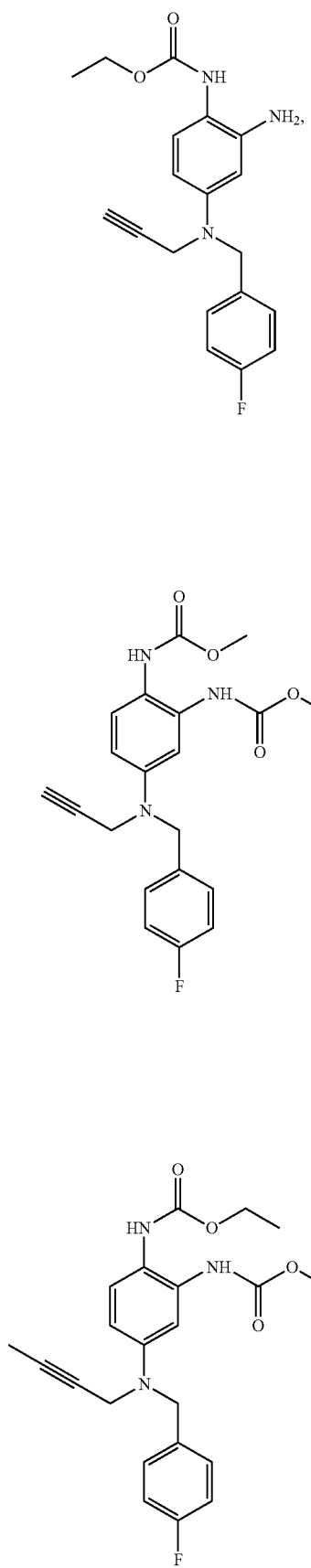
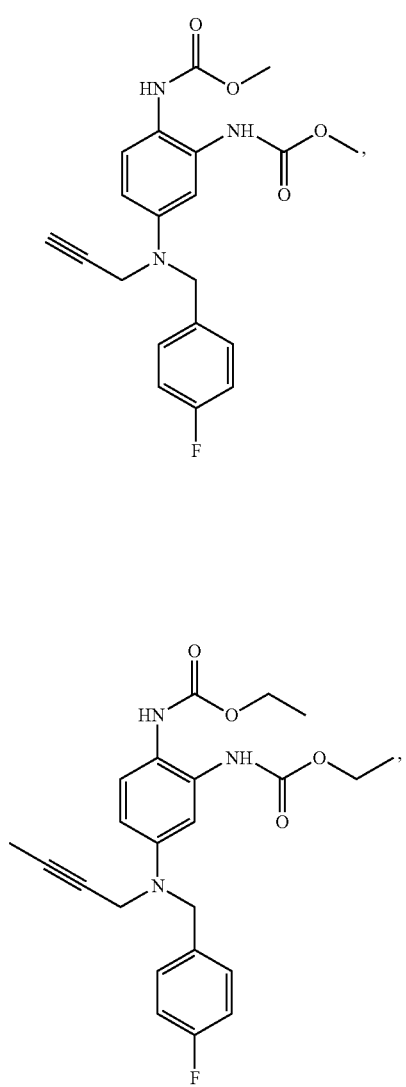
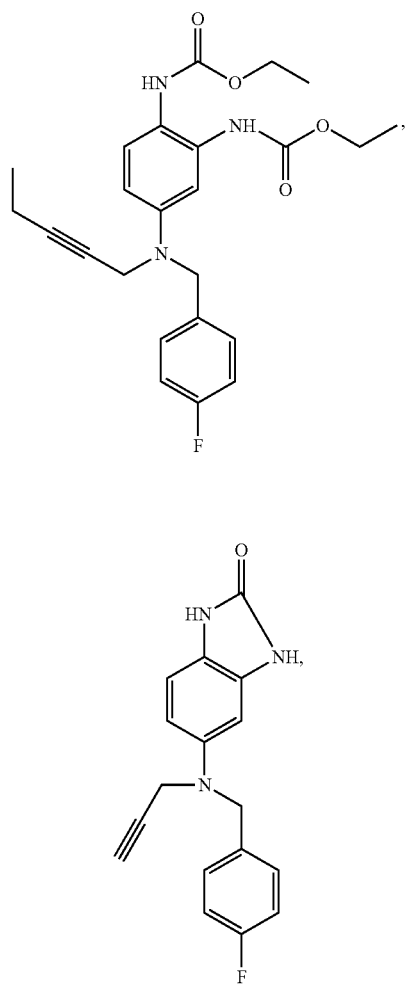
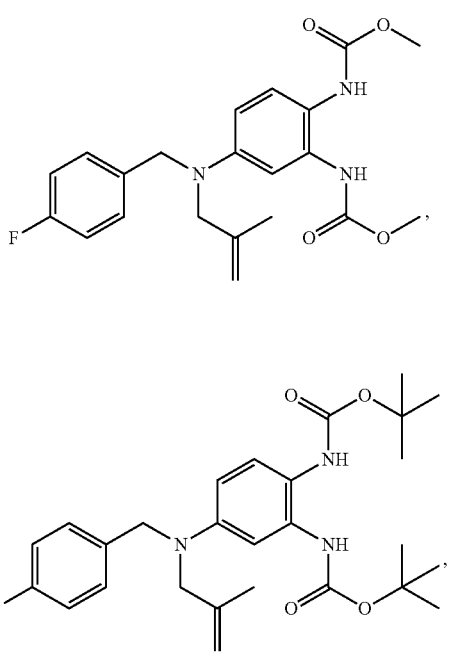

K30 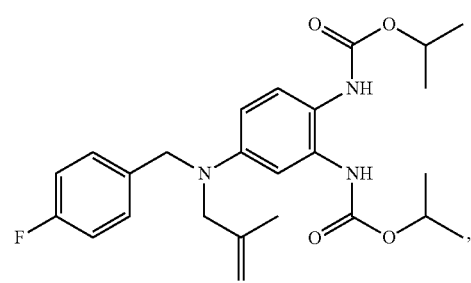
K31 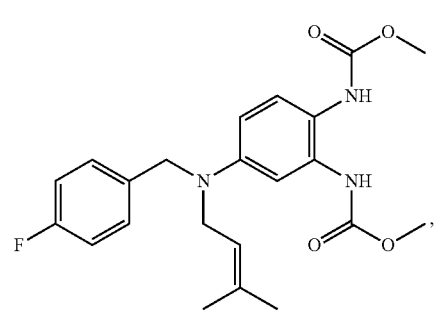
K32 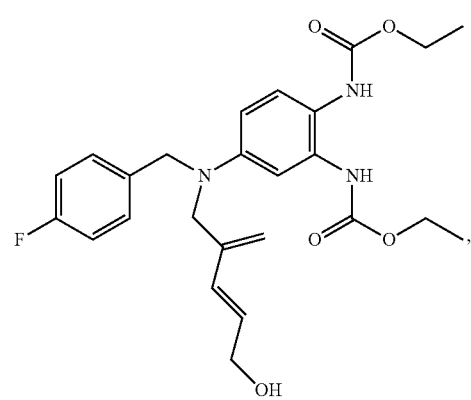
K33 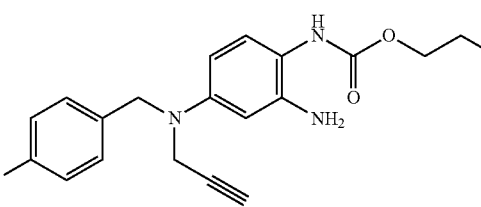
K34 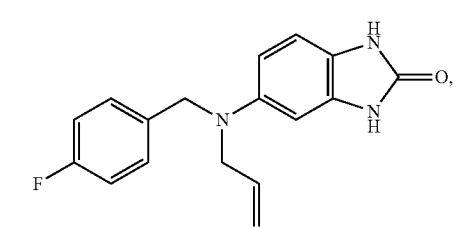
K35 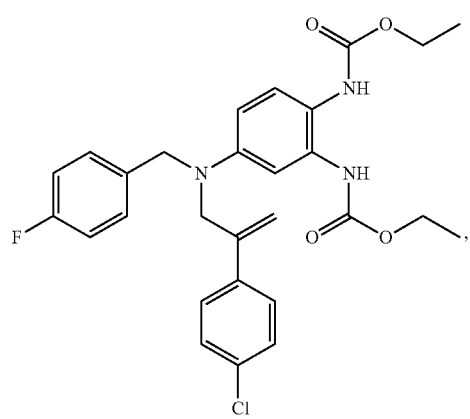
K36 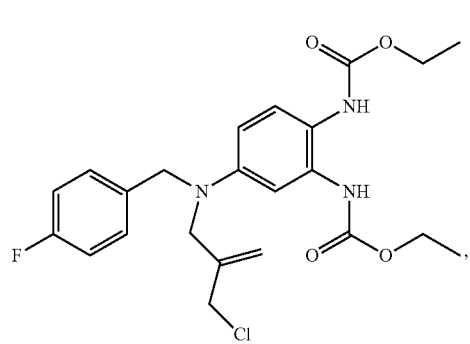
K37 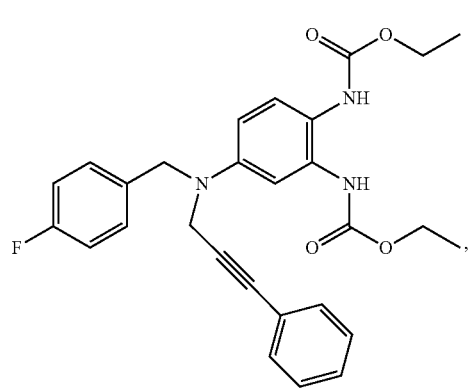
K38 and 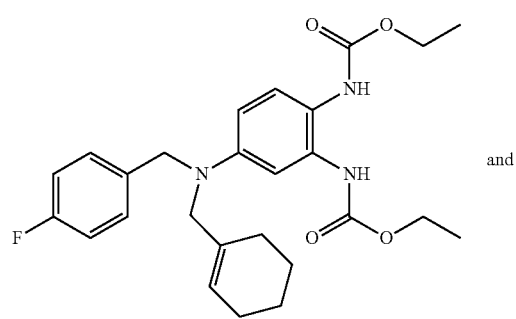

-continued

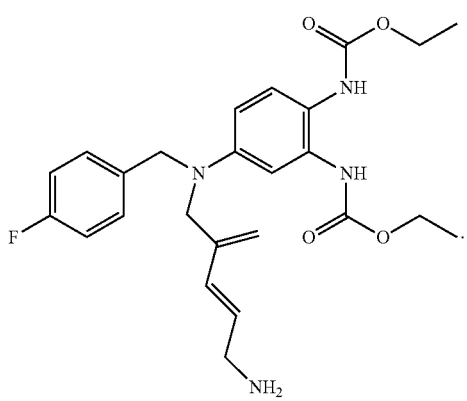

K39

3. The compound or the pharmaceutically acceptable salt thereof according to claim 1, wherein the pharmaceutically acceptable salt of the compound is a salt formed by the compound with an acid, and the acid is selected from the group consisting of maleic acid, succinic acid, citric acid, tartaric acid, fumaric acid, formic acid, acetic acid, propanoic acid, propandioic acid, oxalic acid, benzoic acid, phthalic acid, methanesulfonic acid, benzenesulfonic acid, toluenesulfonic acid, naphthalenesulfonic acid, 1,5-naphthalenedisulfonic acid, camphoric acid, camphor sulfonic acid, salicylic acid, acetyl salicylic acid, aspartic acid, glutamic acid, lactic acid, gluconic acid, ascorbic acid, gallic acid, amygdalic acid, malic acid, sorbic acid, trifluoroacetic acid, taurine, homotaurine, isethionic acid, cinnamic acid, hydrochloric acid, hydrobromic acid, hydroiodic acid, sulfuric acid, nitric acid, phosphoric acid and perchloric acid.

4. A pharmaceutical composition, wherein the pharmaceutical composition comprises the compound or the pharmaceutically acceptable salt thereof according to claim 1 as an active ingredient and pharmaceutically acceptable auxiliary substances.

* * * * *